US009155513B2

(12) United States Patent
Ghosh et al.

(10) Patent No.: US 9,155,513 B2
(45) Date of Patent: Oct. 13, 2015

(54) SYSTEMS AND METHODS FOR DETERMINING HEPATIC FUNCTION FROM LIVER SCANS

(71) Applicant: HEPATIQ LLC, Irvine, CA (US)

(72) Inventors: Dipankar Ghosh, Irvine, CA (US); John Carl Hoefs, Irvine, CA (US)

(73) Assignee: HEPATIQ LLC, Irvine, CA (US)

( * ) Notice: Subject to any disclaimer, the term of this patent is extended or adjusted under 35 U.S.C. 154(b) by 0 days.

(21) Appl. No.: 14/333,370

(22) Filed: Jul. 16, 2014

(65) Prior Publication Data

US 2015/0025372 A1 Jan. 22, 2015

Related U.S. Application Data

(60) Provisional application No. 61/847,313, filed on Jul. 17, 2013.

(51) Int. Cl.
A61B 6/00 (2006.01)
A61B 6/03 (2006.01)
G06T 7/00 (2006.01)

(52) U.S. Cl.
CPC .............. *A61B 6/5205* (2013.01); *A61B 6/032* (2013.01); *A61B 6/037* (2013.01); *A61B 6/469* (2013.01); *A61B 6/481* (2013.01); *A61B 6/50* (2013.01); *A61B 6/5217* (2013.01); *G06T 7/0014* (2013.01); *G06T 2207/10108* (2013.01); *G06T 2207/30056* (2013.01)

(58) Field of Classification Search
None
See application file for complete search history.

(56) References Cited

U.S. PATENT DOCUMENTS

| 8,613,904 | B2 | 12/2013 | Everson et al. | |
|---|---|---|---|---|
| 2005/0276455 | A1* | 12/2005 | Fidrich et al. | 382/128 |
| 2010/0055734 | A1 | 3/2010 | Everson | |
| 2011/0054295 | A1* | 3/2011 | Masumoto et al. | 600/407 |

OTHER PUBLICATIONS

International Search Report and Written Opinion, PCT/US2014/046913, dated Oct. 15, 2014, in 13 pages.
Kavanagh, et al., Automated Volume Determination of the Liver and Spleen From TC-99M Colloid Spect Imaging Quantification of the Liver Functional and Nonfunctional Tissue in Disease, Clinical Nuclear Medicine, vol. 15, No. 7, pp. 495-500, Jul. 1, 1990.

(Continued)

*Primary Examiner* — Unsu Jung
*Assistant Examiner* — Shahdeep Mohammed
(74) *Attorney, Agent, or Firm* — Knobbe Martens Olson & Bear, LLP

(57) ABSTRACT

Systems and methods described herein determine an objective metric for analyzing health of a patient's liver. In some embodiments, the system may include a scanner that can detect radiation counts responsive to administration of radioactive compound to a patient. Further, the system may include an image detection module that can access image data responsive to the detected radiation counts by the scanner. The image detection module can programmatically identify a first region of interest corresponding to a liver of the patient from the image data. A parameter calculator module can programmatically determine a first attribute associated with the first region of interest and calculate a first parameter indicating health of the liver of the patient based at least in part on the first attribute associated with the first region of interest.

16 Claims, 18 Drawing Sheets

(56) References Cited

OTHER PUBLICATIONS

Liu, et al., Quantitative Liver-Spleen Scintigraphy for the Assessment of Diffuse Liver Disease, Ann Nucl Med Sci, vol. 12, pp. 181-187, Jan. 1, 1999.
Pohjonen, et al., Abdominal SPECT/MRI Fusion Applied to the Study of Splenic and Hepatic Uptake of Radiolabeled Thrombocytes and Colloids, Annals of Nuclear Medicine, Japanese Society of Nuclear Medicine, Tokyo, Japan, vol. 10, No. 4, pp. 409-417, Jan. 1, 1996.
"Cost-effectiveness of distal shunt (DSRS) vs. transjugular intrahepatic portosystemic shunt (TIPS)," Sunday Poser Sessions, Portal Hypertension, T.D. Boyer, et al. Oct. 29, 2006 in 3 pages.
"Determinants of the liver-spleen scan image," Hoefs, et al., Hepatology, vol. 8, No. 5, 1988, in 3 pages.
"Quantitative liver function tests predict sustained virologic response to retreatment with peginterferon alfa-2A plus ribavirin: results of the lead-in phase of the halt-C trial," Everson, et al., Hepatology, vol. 40, No. 4, Suppl. 1, 2004, in 2 pages.
"Mortality among individuals tested for Hepatitis C Antibody (anti-HCV) in British Columbia, Canada, 1992-2004," Yu, et al., AASLD 2009 Abstracts, in 3 pages.
"A large spleen volume is protective of ribavirin associated hemolysis in patients with chronic hepatitis C," Sheikh, et al., Gastroenterology, vol. 116, No. 4, May 16-19, 1999, Orlando, FL, in 3 pages.
"Can precise assessment of liver spleen scan parameters predict the course of biliary cirrhosis?," Ocariz, et al., Hepatology, vol. 6, No. 5, Sep.-Oct. 1986, in 2 pages.
"Quantitative shift in $Tc^{99}$ sulfur colloid activity by liver-spleen scan, liver morphology and indocyanine green clearance," Hoefs, et al., Gastroenterology, vol. 88, No. 5, May 1985, in 2 pages.
"Liver-spleen scan reticuloendothelial shift (RES) of sulfur colloid predicts the development of spontaneous bacterial peritonitis," Jonas, et al., Hepatology, vol. 8, No. 5, Sep.-Oct. 1988, in 3 pages.
"Validation of two liver spleen scan techniques for estimating hepatic size," Hoefs, et al., Hepatology, vol. 20, No. 4, Pt. 2, 1994, in 2 pages.
"The perfused hepatic mass estimated from the quantitative liver spleen: before and after transplant," Hoefs, et al., Hepatology, vol. 20, No. 4, Pt. 2, 1994, in 2 pages.
"The impact of spleen volume on sulfur colloid distribution," Hoefs, Hepatology, Oct. 1995, in 2 pages.
"Subjective assessment of reticuloendothelial shift (RES) of sulfur colloid by liver-spleen scan: Correlation with liver and spleen pixel ratio," Hoefs, et al., Hepatology, vol. 8, No. 5, 1988, in 3 pages.
"A simple technique for estimating the functional volume of the spleen," Hoefs, et al., Hepatology, vol. 20, No. 4, Pt. 2, 1994, in 2 pages.
"Prospective prediction of liver disease severity at peritoneoscopy by quantitative liver spleen scan (QLSS)," Hoefs, et al., Hepatology, vol. 20, No. 4, Pt. 2, Oct. 1994, in 2 pages.
"The quantitative liver-spleen scan is the most accurate liver test for CLD," Hoefs, et al., Gastroenterology, vol. 102, No. 4, Part 2, Apr. 1992, in 3 pages.
"Expression of bone marrow activity by liver-spleen scan," Hoefs, et al., Hepatology, vol. 8, No. 5, 1988, in 3 pages.
"Quantitative liver function tests improve the prediction of clinical outcomes in chronic hepatitis C: Results from the hepatitis C antiviral long-term treatment against cirrhosis trial," Everson, et al., Hepatology, Apr. 2012, in 11 pages.
"Functional elements associated with hepatic regeneration in living donors after right hepatic lobectomy," Everson, et al., Liver Transplantation, dated on or after 2006, in 31 pages.
"The spectrum of hepatic functional impairment in compensated chronic hepatitis C: results from the hepatitis C anti-viral long-term treatment against cirrhosis trial," Everson, et al., Alimentary Pharmacology & Therapeutics, 27, 2008 in 12 pages.
"Quantitative tests of liver function measure hepatic improvement after sustained virologic response: results from the HALT-C trial," Everson, et al., NIH, Author Manuscript, Aliment Pharmacol Ther., Mar. 1, 2009, pp. 589-601, in 19 pages.
"Prognostic Value of Ishak Fibrosis State: findings from the HALT-C trial," Everhart, et al., NIH Public Access, Author Manuscript, Hepatology, vol. 51, Feb. 2010, in 19 pages.
"Perfused kupffer cell mass," Hoefs, et al., Digestive Diseases and Sciences, vol. 40, No. 3, Mar. 1995), pp. 552-560, in 9 pages.
"The liver-spleen scan as a quantitative liver function test: Correlation with liver severity at peritoneoscopy," Hoefs, et al., Hepatology, Oct. 1995, in 9 pages.
"Rate of progression of hepatic fibrosis in patients with chronic hepatitis C: results from the HALT-C trial," Hoefs, et al., NIH Public Access, Author Manuscript, Gastroenterology, Sep. 2011, pp. 900-908, in 19 pages.
"Factors affecting the quantitative liver-spleen scan in normal individuals," Hoefs, et al., Digestive Diseases and Sciences, vol. 50, No. 2, Feb. 2005, pp. 283-289, in 7 pages.
"A novel, simple method of functional spleen volume calculation by liver-spleen scan," Hoefs, et al., The Journal of Nuclear Medicine, 1999, pp. 1745-1755, in 12 pages.
"Functional measurement of nonfibrotic hepatic mass in cirrhotic patients," Hoefs, et al., The American Journal of Gastroenterology, vol. 92, No. 11, 1997, in 7 pages.
"Mechanism for the abnormal liver scan in acute alcoholic liver injury," Hoefs, et al., The American Journal of Gastroenterology, vol. 79, No. 12, 1984, in 10 pages.
"The abnormal hepatic scan of chronic liver disease: Its relationship to hepatic hemodynamics and colloid extraction," Horisawa, et al., Gastroenterology, vol. 71, No. 2, pp. 210-213, 1976, in 6 pages.
"Quantitative liver-spleen scan using single photon emission computerized tomography (SPECT) for assessment of hepatic function in cirrhotic patients," Zuckerman, et al., Journal of Hepatology, vol. 39, 2003, pp. 326-332, in 7 pages.

* cited by examiner

SYSTEMS AND METHODS FOR DETERMINING HEPATIC FUNCTION FROM LIVER SCANS

CROSS-REFERENCE TO RELATED APPLICATIONS

The present application claims the benefit of U.S. Provisional Patent Application No. 61/847,313, filed Jul. 17, 2013, the disclosure of which is hereby incorporated by reference in its entirety.

BACKGROUND

Chronic liver disease is characterized by the gradual buildup of scar tissue (fibrosis) in response to many forms of chronic hepatic inflammation. This can lead to cirrhosis with a decrease in hepatic function. Liver biopsy is one of the most common methods of detecting a liver's health. The biopsy is, however, invasive as it requires removing a portion of the liver for analysis. Furthermore, liver biopsy analysis is subjectively scored and may also vary depending on the location of biopsy.

SUMMARY

The systems and methods described herein can be implemented by a computer system comprising computer hardware. The computer system may include one or more physical computing devices, which may be geographically dispersed or co-located.

Certain aspects, advantages and novel features of the inventions are described herein. It is to be understood that not necessarily all such advantages may be achieved in accordance with any particular embodiment of the inventions disclosed herein. Thus, the inventions disclosed herein may be embodied or carried out in a manner that achieves or selects one advantage or group of advantages as taught herein without necessarily achieving other advantages as may be taught or suggested herein.

In certain embodiments, a system for detecting a liver health parameter of a patient can include a single photon emission computed tomography (SPECT) scanner that can obtain image data of organs of a living patient, including a liver and a spleen of the patient. The SPECT scanner can obtain the image data by at least detecting radiation counts responsive to administration of a radioactive compound to the patient. The system can further include a memory device including an image detection module and a parameter calculator stored thereon as computer-executable instructions. The system can further include a hardware processor that can implement the image detection module by executing the computer-executable instructions to at least access the image data output by the scanner. The instructions may further include programmatically identify a first region of interest corresponding to the liver of the patient from the image data, the first region of interest comprising a bounded region around the liver of the patient and being indicative of a size of the liver, wherein the size of the liver is correlated with a health condition of the liver, such that a size of the first region of interest is indicative at least in part of the health condition of the liver. In some embodiments, the instruction can further include programmatically identify a second region of interest corresponding to a spleen of the patient from the image data. Additionally, the hardware processor may also implement the parameter calculator by executing computer-executable instructions to at least programmatically determine a first attribute associated with the first region of interest. The instructions can further include programmatically determine a second attribute associated with the second region of interest. In addition, the instructions can include calculate a first parameter indicative of the health condition of the liver of the patient based at least in part on the first attribute associated with the first region of interest and the second attribute associated with the second region of interest. In some embodiments, the instructions can include output, in a computer-generated graphical user interface, an indication of the first parameter for presentation to a clinician, enabling the clinician to make a clinical care decision for the patient.

The system of the preceding paragraph can have any subcombination of the following features: wherein the first parameter includes perfused hepatic mass; wherein the first attribute includes a representation of radiation counts in the first region of interest; wherein the image detection module can compare a geometric property of the first region of interest relative to the second region of interest; wherein the memory further includes a user interface module that can include additional instructions configured to generate and output a second user interface, the second user interface can provide functionality for the clinician to input a command to modify the first region of interest; wherein the image detection module can combine a plurality of frames from the image data, said frames corresponding to planes transverse to the patient's body; wherein the image data includes a plurality of frames; wherein the image detector module can programmatically detect the first region of interest from a first frame and programmatically detect the second region of interest from a second frame, wherein said first frame corresponds to a different plane with respect to the patient's body than the second frame; wherein the graphical user interface includes a display of the first region of interest.

Additionally, in certain embodiments, a method for detecting a liver health parameter of a patient can include receiving image data comprising a representation of detected radiation counts corresponding to one or more organs of a patient. The method can also include programmatically identifying a first region of interest corresponding to a liver of the patient from the image data. In addition, the method can include programmatically identifying one or more additional regions of interest corresponding to one or both of a spleen of the patient and marrow of the patient from the image data. Further the method can include determining a first parameter indicative of health of a patient based at least in part on a first attribute associated with the first region of interest and optionally also based on a second attribute associated with the second region of interest. In some embodiments, the method can include programmatically generating an output responsive to the first parameter for presentation to a clinician, wherein the output comprises one or more of a value of the first parameter and a health report associated with the first parameter. In some embodiments, at least said programmatically identifying a first region of interest corresponding to a liver of the patient from the image data is performed under control of processing electronics.

The method of the preceding paragraph can have any subcombination of the following features: wherein the first parameter includes perfused hepatic mass; wherein the first attribute includes a representation of radiation counts in the first region of interest; further including detecting a first centroid associated with the first region of interest and detecting a second centroid associated with the second region of interest; further including programmatically identifying a third region of interest based at least in part on the detected first and second centroids.

In certain embodiments, a system for detecting a liver health parameter of a patient can include a hardware processor. The system can receive scanner output data responsive to detected radiation from a radiation detecting scanner, said scanner output data responsive to a radioactive compound administered to a patient. The system can further apply image processing techniques to detect two or more separate tissue masses in the scanner output data, at least one of the two or more separate tissue masses corresponding to an organ selected from a group consisting of a liver and a spleen. The system can also determine a parameter corresponding to function of one or more of the two or more separate tissue masses of the patient. In some embodiments, the system can output a graphical indication of the parameter for presentation on a display.

The system of the preceding paragraph can have any subcombination of the following features: wherein the system can further detect a bone marrow region based at least in part on the detected one or more organs; wherein the parameter includes one of a liver volume, a spleen volume, a perfused hepatic mass, a total count ratio, a staging indicator, an estimated peritoneoscopic score, a normalized liver volume, a normalized spleen volume, a highest average concentration, liver counts, a liver spleen index, a liver bone marrow index, a liver length, a spleen length, spleen counts, bone marrow counts, and a hepatic activity index; wherein the scanner output data includes at least one of or more frames corresponding to images of the patient in a plane transverse to a long axis of the body of the patient; wherein the system can further combine a plurality of frames from the image data, said frames corresponding to planes transverse to a long axis of the body of the patient.

BRIEF DESCRIPTION OF THE DRAWINGS

Embodiments disclosed herein are described below with reference to the drawings. Throughout the drawings, reference numbers are re-used to indicate correspondence between referenced elements. The drawings are provided to illustrate embodiments of the inventions described herein and not to limit the scope thereof.

DETAILED DESCRIPTION OF SPECIFIC EMBODIMENTS

I. Introduction

Figure 1:
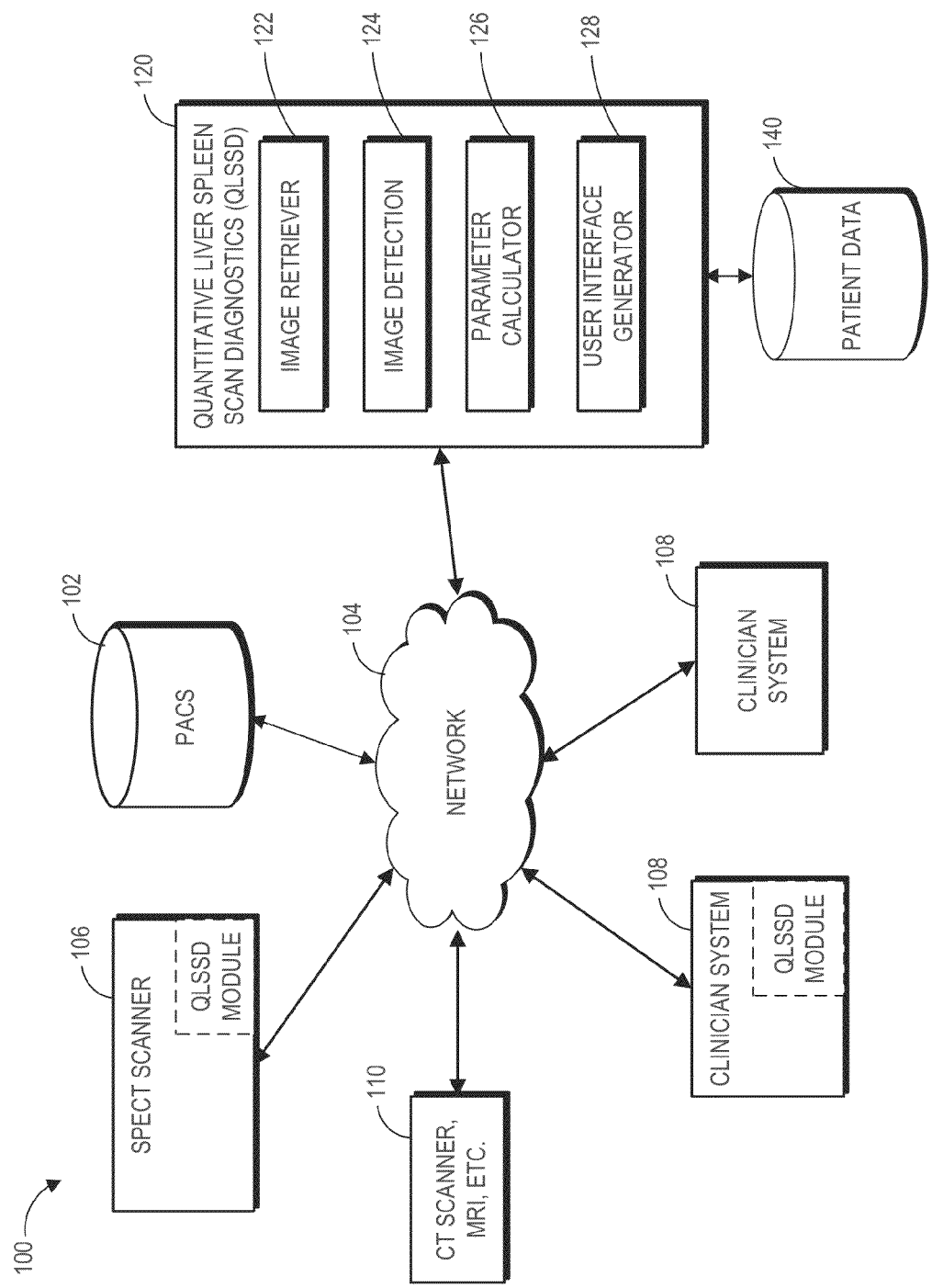
FIG. 1 illustrates an embodiment of a computing environment including a quantitative liver spleen scan diagnostics (QLSSD) system that can enable clinicians to quantitatively analyze health of a patient's liver.

The liver is a vital organ with a wide range of functions, including filtering blood coming from the digestive track before passing it to the rest of the body. The liver also detoxifies chemicals and metabolizes drugs. Diseases can reduce the functionality of the liver. Long-term damage to the liver from any cause can lead to permanent scarring, called cirrhosis. Assessing health of a liver is critical in order to predict prognosis and for treatment of patients. A liver biopsy is most commonly used test to determine hepatic functionality. But, the test is invasive and subjective, depending on the analyzing clinician. The results may also depend on the location of the biopsy. Furthermore, the decrease in hepatic function relates more to a patient's health than information gathered from routine blood tests or even fibrosis. Accordingly, in some embodiments, the system described herein can generate quantitative measurement of hepatic function. In addition to its ordinary meaning, hepatic can mean of or pertaining to function of the liver. The hepatic function can correspond to healthiness or functionality of liver.

Non-invasive method of detecting health of a patient's liver can include analyzing images generated by a Single Photon Emission Computed Tomography (SPECT) scanner. The SPECT scanners can generate images responsive to administrating radioactive compound to patients. Because one of the functions of the liver is to filter blood, the radioactive compound is filtered by the liver and the SPECT scanner can pick the radiation counts to detect absorption of the radioactive compound. The absorption depends on the health of the liver. A healthy liver absorbs the majority of the compound, and the radiation detected by the scanner may mostly be concentrated in the liver. However, when the liver is diseased, more of the radioactive compound can leak out of the liver and flow into, for example, the spleen and/or bone marrow. Accordingly, the radioactive counts from the SPECT scan responsive to absorption of the compound can indicate hepatic function.

Abstracting information from the image scans can be difficult. The analysis may change for different SPECT scanners. Further, significant training might be required for clinicians to determine parameters from the images. In addition, the analysis may suffer from subjective determinations of clinicians (who may, for example, hand-draw regions of interest as described more in detail below). The regions of interests (ROIs) calculated using a QLSSD system (discussed below)

can be robust compared to hand drawn ROIs. For instance, there may be variations in hand drawn ROIs between different clinician. Moreover, it may be cumbersome and time-intensive to hand draw ROIs. Also, the clinicians may not be able to detect counts appropriately from the image as it may depend on the contrast levels of images and may vary between scanners. In some instances, splenectomy, liver-spleen overlap, and anatomical variability may also increase the difficulty in analyzing SPECT images for the clinicians. Accordingly, the QLSSD system can diagnose and identify stages of chronic liver diseases based on the image scans.

This disclosure describes embodiments of a quantitative liver spleen scan diagnostics (QLSSD) system that can provide clinicians a tool to determine a patient's health based on characterization of the patient's liver through one of the scanning techniques, e.g. from a SPECT scanner. In some embodiments, the QLSSD system can calculate one or more numerical parameters that may be correlated with the patient's liver health. The QLSSD system can also generate text or graphical impressions based on the calculated numerical parameters to report results based on the scans.

II. Example QLSSD System

FIG. 1 illustrates an embodiment of a computing environment 100 for providing clinicians with access to QLSSD system 120 to determine a patient's health based on analyzing scans of the patient's organ. In an embodiment, the QLSSD system 120 determines the patient's health based on analyzing images of liver from a SPECT scanner. The computing environment 100 can include clinician systems 108 that can access the QLSSD system 120, which may include one or modules to determine the patient's hepatic function.

For instance, the QLSSD system 120 can include an image retriever module 122 that can retrieve images corresponding to scans of a body part, e.g. liver. In an embodiment, the image retriever 122 can receive raw images directly from the SPECT scanner 106. In other embodiments, the image retriever 122 can receive images from a PACS (Picture Archiving and Communication System) repository 102. The image retriever 122 can also receive images from a storage medium such as a compact disc (CD), a portable hard drive, etc. The PACS system 102 may store images in a DICOM (Digital Imaging and communication in Medicine) format. The PACS system 102 may also include other non-image data regarding patients. The image retriever 122 can also receive images of different formats (e.g. jpeg, png, pdf, bmp, CT scanner raw files, MRI raw files, PET raw files, x-ray raw files, etc.). In an embodiment, the image retriever 122 retrieves images from the PACS or SPECT scanner over a network 104. The image retriever 122 may get the images from PACS 102 in response to an input from clinician system 108. In some embodiments, the image retriever may automatically receive the images from the SPECT scanner 106 after a predetermined time interval.

The QLSSD system 120 can include an image detection module 124 to analyze the images retrieved by the image retriever 122. The image detection module 124 can process the images and identify one or more regions of interests (ROI) from the images as described more in detail below. The regions of interests can include organs, tissues, tissue masses, bones, etc. In an embodiment, the ROI can include a region corresponding to a patient's liver. The image detection module 124 can process images generated by SPECT scanner. In some embodiments, the image detection module 124 can also process images produced from a CT scanner or a MRI machine or from another type of scanner. The image detection module 124 can use information obtained from one type of image to process another type of image for the same patient. For instance, the image detection module 124 can use information detected from CT scan of the patient to detect regions of interest in the SPECT scans. The image detection module 124 may store analyzed images in patient data repository 140 or transmit it back to PACS 102. In some embodiments, the image detection module 124 may include internal checks to ensure that the ROI corresponds to the particular organ. If the detection module 124 determines that the detected ROI does not accurate reflect a particular organ, then it can give clinicians an option to override the automatic ROI detection as described more in detail below.

The parameter calculator 126 of the QLSSD system 120 can determine one or more attributes from the region of interests identified by the image detection module 124. For instance, the parameter calculator 126 can determine a length of a region of interest corresponding to the spleen. The parameter calculator 126 can also determine a volume or concentration corresponding to a region of interest in terms of total counts or voxels. In an embodiment, a voxel represents a value (e.g. radiation count) in a three dimensional space. In some embodiments, the parameter calculator 126 can calculate parameters corresponding to health of a liver. Some of the example parameters include Perfused Hepatic Mass (PHM), Hepatic Activity Index (HAI), Total Counts Ratio (TCR), Normalized Liver Volume (NLV), and Normalized Spleen Volume (NSV). These parameters may quantitatively indicate hepatic function. The calculated parameters can be stored in the patient data repository 140. In some instances, the calculated parameters can be transmitted and stored in PACS along with other data for that patient. The parameters can also be transmitted over a network to a clinician system. The parameter calculator 126 can also generate a trend based on stored parameters to allow clinicians to monitor health of patients over time.

The user interface module 128 can interact with one or more other modules of the QLSSD system 120 to generate one or more graphical user interfaces. In some embodiments, the user interfaces can be one or more web pages or electronic documents. The user interface module 128 can also receive data such as patient information from the clinician systems 108. In some instances, the user interface module 128 may receive commands from the clinician systems 108 to initiate one or more functionalities of the QLSSD system. The data can be stored by patient data repository 140. Embodiments of user interfaces are described in detail below.

The QLSSD system 120 can be implemented in computer hardware and/or software. The QLSSD system 110 can execute on one or more computing devices, such as one or more physical server computers. In implementations where the QLSSD system 110 is implemented on multiple servers, these servers can be co-located or can be geographically separate (such as in separate data centers). In addition, the QLSSD system 110 can be implemented in one or more virtual machines that execute on a physical server or group of servers. Further, the QLSSD system 110 can be hosted in a cloud computing environment, such as in the Amazon Web Services (AWS) Elastic Compute Cloud (EC2) or the Microsoft® Windows® Azure Platform. The QLSSD system 110 can also be integrated with scanners 106 and 110 through software or hardware plug-in or an API (application programming interface). In some embodiments, the clinician systems 108 may implement some or all of the modules of the QLSSD system 120. For instance, the clinician systems 108 may implement the user interface generator module 128, while the rest of the modules are implemented remotely on a server. In other embodiments, a plugin to the QLSSD system 110 may be installed on to a third party tool.

The clinician systems 108 can remotely access the QLSSD system 110 on these servers through the network 104. The clinician systems 108 can include thick or thin client software that can access the QLSSD system 110 on the one or more servers through the network 104. The network may be a local area network (LAN), a wide area network (WAN), such as the Internet, combinations of the same, or the like. For example, the network 104 can include a hospital's private intranet, the public Internet, or a combination of the same. In some embodiments, the user software on the clinician system 108 can be a browser software or other application software. The clinician system 108 can access the QLSSD system 110 through the browser or application software.

In general, the clinician systems 108 can include any type of computing device capable of executing one or more applications and/or accessing network resources. For example, the clinician systems 108 can be desktops, laptops, netbooks, tablet computers, smartphones, smartwatches, augmented reality wear, PDAs (personal digital assistants), servers, e-book readers, video game platforms, television set-top boxes (or simply a television with computing capability), a kiosk, combinations of the same, or the like. The user systems 108 include software and/or hardware for accessing the QLSSD system 110, such as a browser or other client software.

III. Organ Health Detection Process

Figure 2:
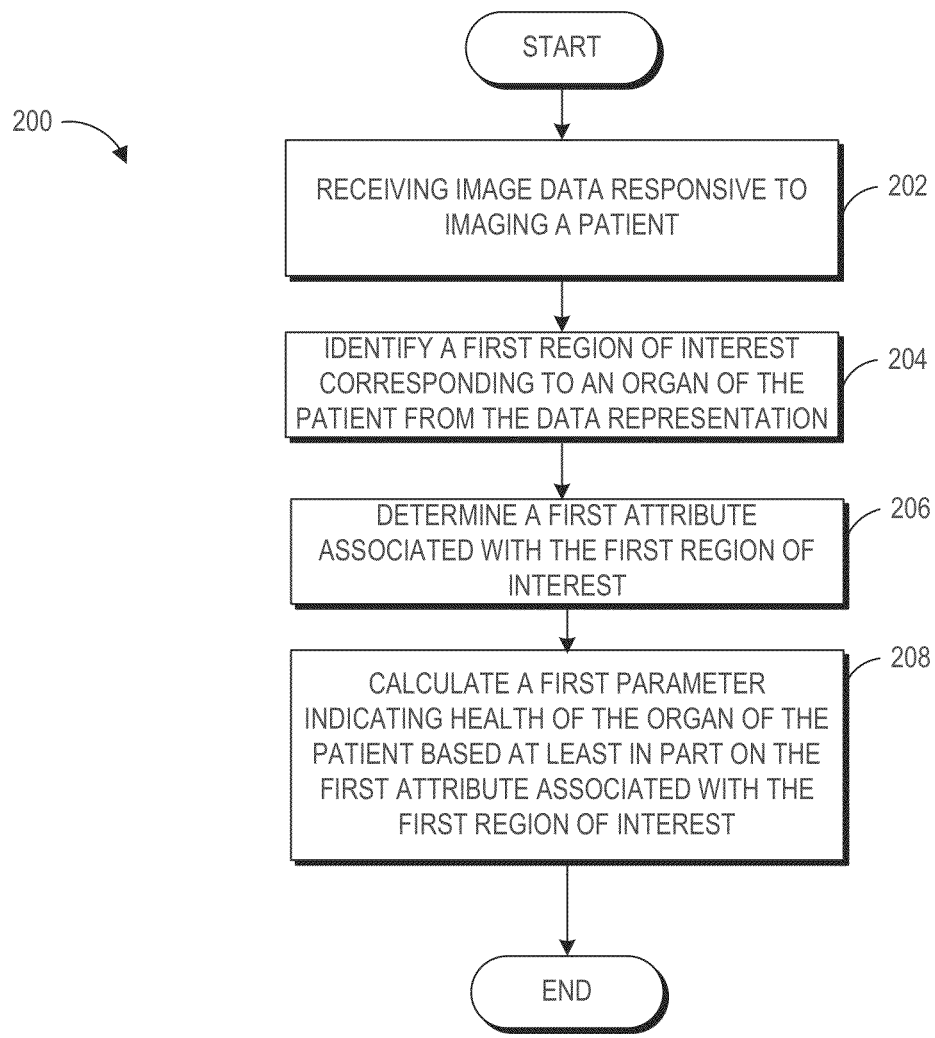
FIG. 2 illustrates an embodiment of an organ health detection process.

FIG. 2 illustrates an embodiment of an organ health detection process 200 for calculating a parameter corresponding to the health of the organ (or more generally a mass of tissue). The parameter can be a numerical, graphical, or textual indicator. The organ health detection process can be implemented by the system described above. For illustrative purposes, the process 200 will be described as being implemented by components of the computing environment 100 of FIG. 1. The process 200 depicts an example overview of calculating a parameter based on scanned images of a patient.

The process 200 can begin at block 202 with receiving image data responsive to imaging a patient. The image retriever module 122 can receive image data corresponding to SPECT, CT, or MRI scans of the patient's organ. The received images may include one or more anatomical features (e.g. liver, spleen, bone marrow, etc.). The image detection module 124 can automatically detect these anatomical features using one or more object detection techniques (e.g. morphology, edge detection, centroid search, histogram, etc.) at block 204.

The detected anatomical features can be used to extract quantitative information from the image scan. For example, at block 206, the parameter calculator 126 can calculate an attribute associated with the detected anatomical feature. In an embodiment, the detected anatomical feature can include a spleen, and the corresponding attribute can be the length of the spleen. A more detailed example with respect to liver and spleen will be discussed below with respect to FIGS. 3 and 4. The parameter calculator 126 can further determine an indicator or a parameter associated with the health of the detected anatomical features or the health of the patient at block 208. In one embodiment, the indicator includes Perfused Hepatic Mass (PHM), which may directly correlate with hepatic function or healthiness of the liver. The PHM can be a numerical indicator or graphical output based on a numerical indicator and may provide an objective standard to determine a patient's liver health.

The process 200 can be used to determine a parameter corresponding to health of different anatomical features of a patient. As discussed above, the process 200 can be used to determine a parameter corresponding to hepatic function. In another example, the process 200 can be used to determine a parameter corresponding to a patient's heart or cardiac output, pulmonary nodule classification, or kidney function, or function of any other organ or tissue mass of a patient.

IV. Liver Health Detection Process

Figure 3:
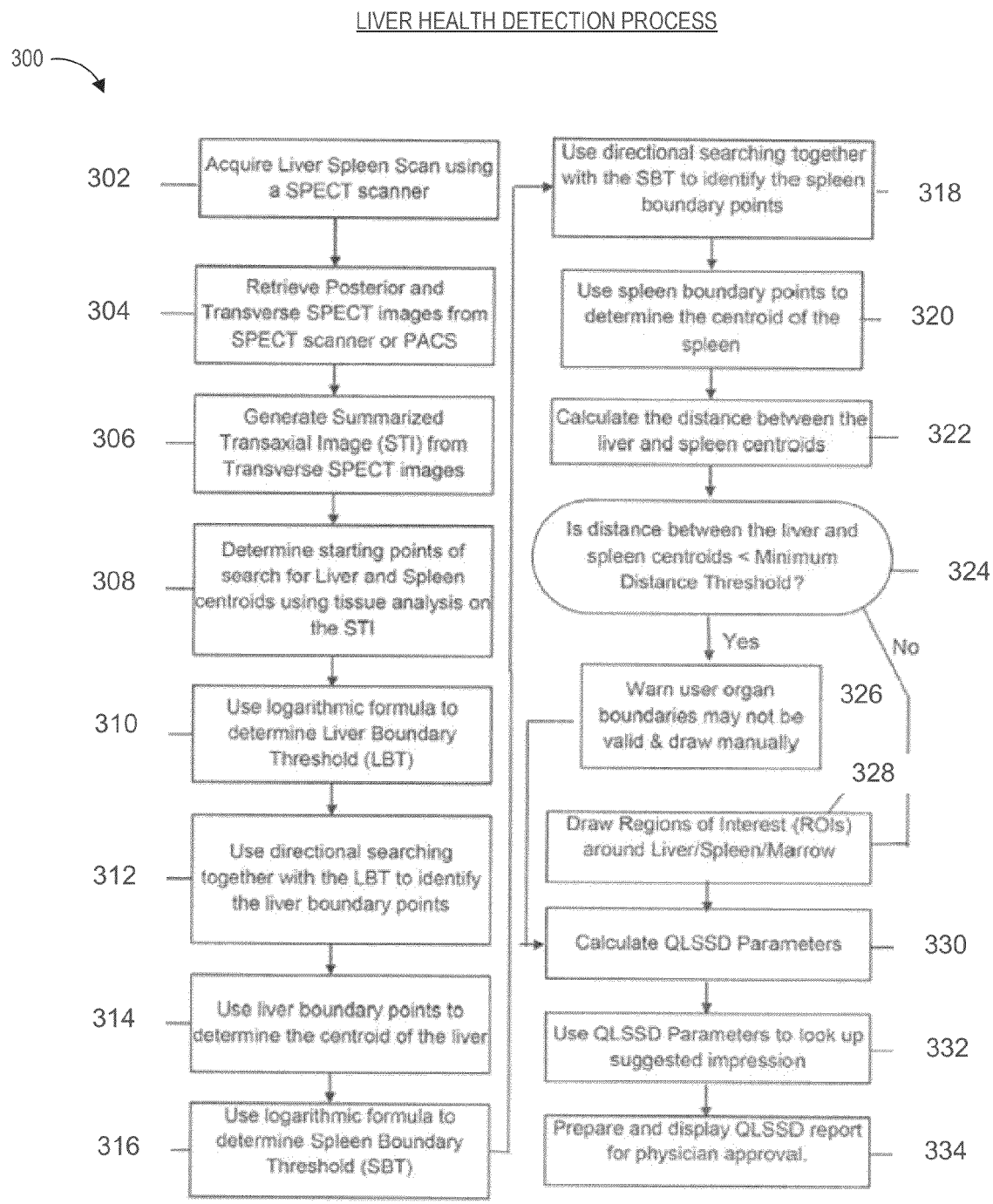
FIG. 3 illustrates an embodiment of a liver health detection process.

FIG. 3 illustrates a more specific example process 300 of the organ health detection process 200 described above. The process 300 can enable clinicians to obtain a parameter corresponding to healthiness of the patient's liver. The liver health detection process 300 can be implemented by the system described above. For illustrative purposes, the process 300 will be described as being implemented by components of the computing environment 100 of FIG. 1. The process 300 depicts an example overview of calculating a parameter associated with hepatic function using scanned SPECT images of a patient.

Figure 6:
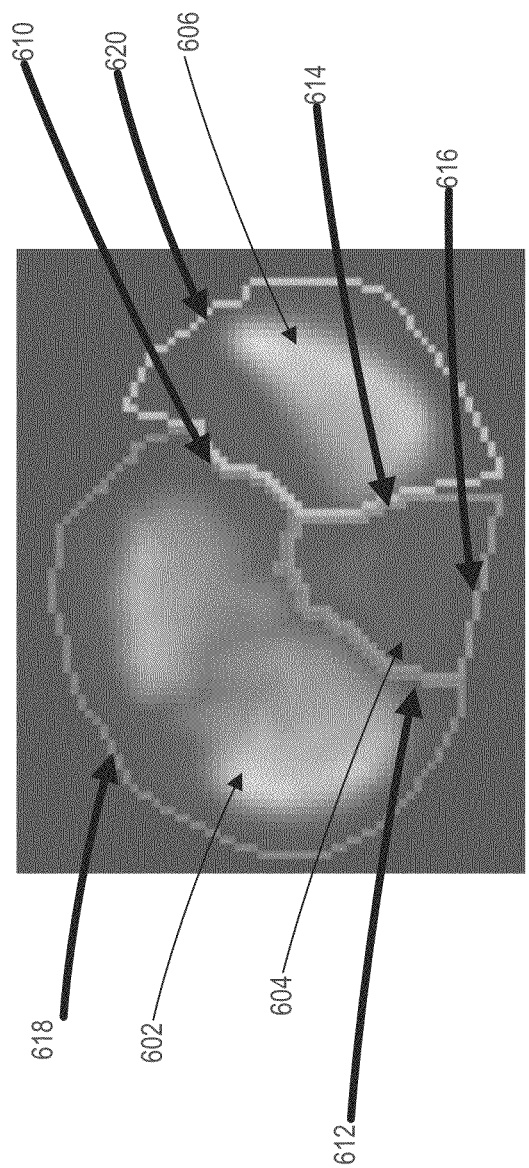
FIG. 6 illustrates liver, spleen, and bone marrow ROI detected from the SPECT scan.

The process 300 may begin with acquiring scanned images from a SPECT scanner at block 302. The SPECT scanner generates images by measuring radiation counts responsive to administrating radioactive compound to a patient. In an embodiment, the images are generated 30 minutes after administration of the compound. The time may vary between patients, but typically it takes about half an hour for the radioactive compound (e.g. Technetium-99 metastable) to be filtered from the blood by the liver. For a patient with a healthy liver, most of the radioactive compound will be found in the liver. However, in a diseased liver, the compound can leak into the spleen and bone marrow. Since most of the compound may be found in the liver, spleen, bone marrow (near vertebrae) region, the SPECT scanner output can provide mechanism for separating liver, spleen, and bone marrow from rest of the organs. An example summarized transaxial SPECT scan of liver, spleen, and bone marrow is shown in FIG. 6.

As discussed above, the scanned images can be received directly from the scanner or via PACS. The image retriever module 122 can automatically process the received images depending on the source at block 304. The received images can include multiple orientations. In one embodiment, the image retriever module 122 can retrieve planar posterior and transverse SPECT images from SPECT scanner or PACS. The transverse SPECT images may include one or more frames corresponding to planes perpendicular to the long axis of the patient's body. The planar posterior images may include one or more frames taken from the perspective of the patient's backside and may correspond to planes parallel to the long axis of the patient's body. Other image views include anterior, oblique, sagittal, coronal, reformatted, secondary captures, or derived images. In some embodiments, the image retriever module 122 can directly process raw scanner data instead of image data. The received images may be divided into multiple frames spanning an area of the patient's body. Accordingly, the received images can include a three dimensional perspective of the SPECT scan.

The image detection module 124 can process the received images at block 124. In an embodiment, the image detection module 124 can generate a combined transaxial image (CTI) from the transverse liver-spleen images obtained from the SPECT scanner at block 306. In an embodiment, the CTI is a summarized transaxial image (STI), which can be a combination or a sum of each of the transaxial images covering the liver-spleen area. In other embodiments, the CTI is generated using through voxel-by-voxel averaging of the transverse images. Other methods for generating CTI that can be used include using median, mode, maximum intensity, auto-correlation, and similar statistical techniques. In an embodiment, maximum intensity transaxial image (MITI) is detected by selecting the highest intensity pixel at (x,y) from some or all the transaxial images covering the liver-spleen area. Accordingly, the final MITI may have highest intensities from some or all the transaxial images for each pixel. In some embodiments, MITI can provide a better contrast than STI. The image detection module 124 can combine the transaxial images before detection of region of interests. In some embodiments, the regions of interests may be detected prior to combination of frames.

Figure 5:
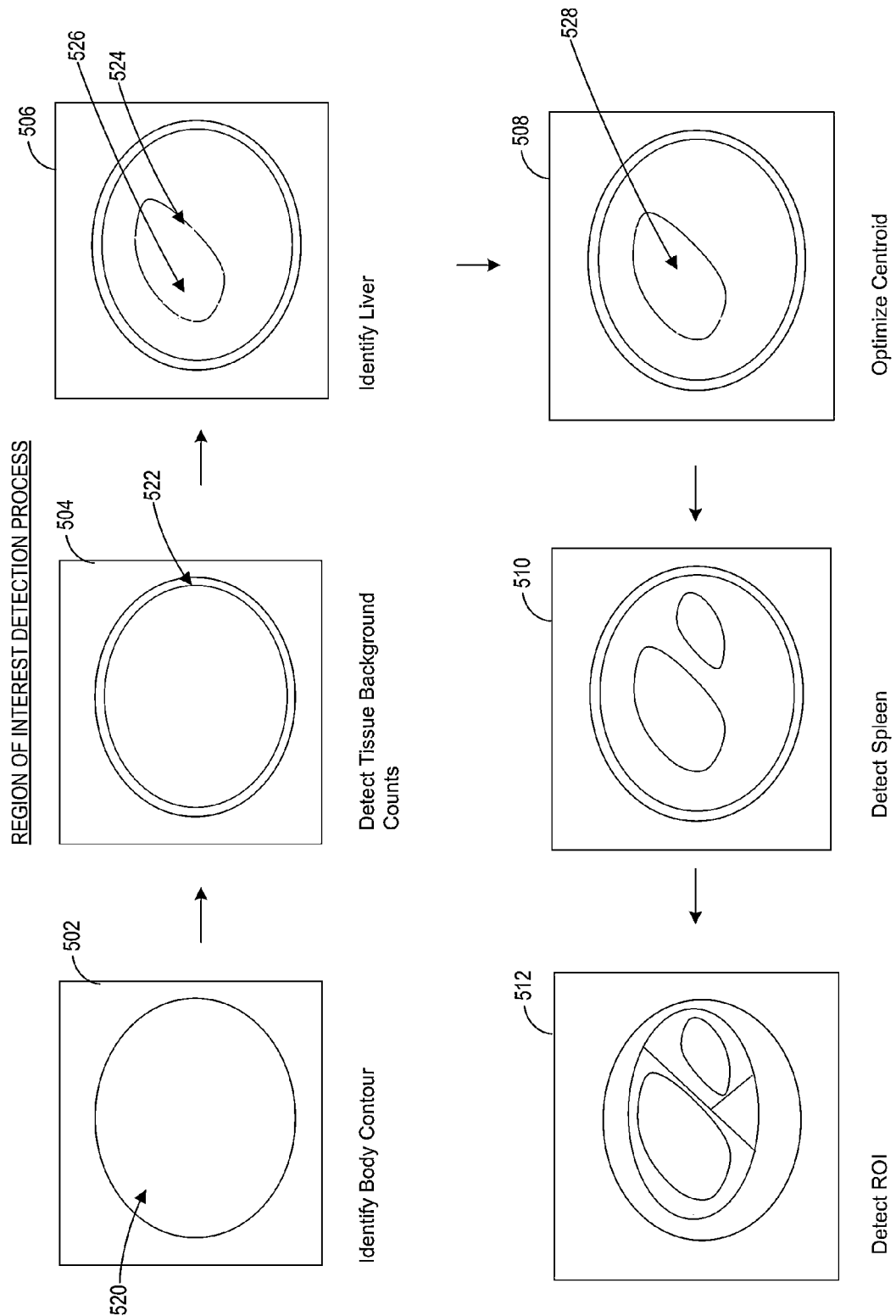
FIG. 5 illustrates an example graphical representation of the embodiment of processes described with respect to FIGS. 3 and 4.

The image detection module 124 can use the CTI to detect regions of interests. The regions of interest can correspond to anatomical features of the patient. In an embodiment, the image detection module 124 detects liver, spleen and bone marrow. The image detection module 124 can locate the liver based on a comparison of intensities in the CTI. FIG. 5 illustrates a simplified diagram to show the steps for detecting and separating liver, spleen and bone marrow ROIs.

The image detection module 124 can select frame boundaries and conduct directional searching to locate the liver. At block 308, the image detection module 124 can identify a body contour 520 as shown in step 502 in FIG. 5 by comparing intensities. In general, counts will be near zero outside of the body. A healthy liver will include much higher intensity counts than surrounding tissue. Even a diseased liver may include at least some portions with high intensity counts.

At block 310, the image detection module 310 can determine liver boundary threshold. Step 504 of FIG. 5 illustrates an example for determining liver boundary threshold. The image detection module 124 can identify a border region 522 around the body contour 520 to determine the threshold. In an embodiment, the threshold is the average pixel intensity in the border region or some other value. The threshold can also be the maximum or minimum pixel intensity in the border region. In some embodiments, the threshold can be determined using a logarithmic formula.

Using the threshold value, the image detector 310 can use directional searching to locate a region of interest corresponding to the liver at block 312. As an example, the image detector 124 can select the north-west corner of the body contour (although any other starting region may be selected) and move across the rows and columns of pixels to determine when the intensity count exceeds the threshold. Accordingly, the image detector 310 can find a pixel location that exceeds the threshold value indicating that the pixel is most likely inside the liver. In one embodiment, a value of 20% above the tissue threshold is used. After finding the pixel location, the image detection module 124 can implement a directional searching to identify the boundary points of the liver. As shown in step 506 of FIG. 5, the image detector 124 can search along eight directions in a star pattern from the pixel location (526). In other embodiments, the image detector 124 can also implement other methods of searching, e.g. 16-point star, etc. The boundary points can be identified by comparing intensities of pixels with the threshold value as discussed above. In some embodiments, the image detection module 124 can also use sampling to identify boundary points of the liver.

Accordingly, the image detector 124 can identify (for example) 8 boundary points of the liver. At block 314, using these boundary points, the image detector 124 can calculate a first centroid location. In some embodiments, the image detector 124 can quickly locate the centroid of the organ without using trigonometric calculations by using straight combinations of matrix indices. For example, the matrix indices may be combined using summations. After finding the first centroid, the image detector 124 can repeat the process to locate the second centroid using directional searching from the first centroid location. In some embodiments, the image detector can rotate the star search direction. For example, the rotation angle can be offset by 10 degrees in between centroid search. The eight point star search may be repeated multiple times until the location of the centroid appears to converge. In some embodiments, the number of iterations can be fixed. Step 508 of FIG. 5 illustrates the final centroid location 528. Accordingly, the image detector 124 can identify boundary points of the liver and the centroid of the liver.

In blocks 316 to 318 of the process 300, the boundary points and the centroid of spleen can be identified in a similar manner as discussed above with respect to the liver. In most patients, the spleen is located in a south-east direction relative to the liver. Thus, the image detector module 124 can conduct a similar search from the south-east corner of the body contour 520 to identify the spleen boundary points and centroid. Step 510 of FIG. 5 illustrates both the liver 524 and the spleen 530.

The image detector 124 can automatically validate the detected liver and spleen. At block 324, the image detector 124 can calculate the distance between the liver and spleen centroids and compare with an acceptable range to validate the detected liver and spleen. If the distance is not within a range, e.g., it is less than the minimum or more than the maximum value, the image detector can notify one or more modules of the QLSSD system 120. The QLSSD system 120 can notify the clinician systems that organ detection might have failed and may give an option to the clinician to manually draw the ROIs. The user interface generator module 128 can generate user interfaces for the clinician to draw the ROIs.

The image detector 124 can also validate for overlaps. For instance, if the liver and spleen regions overlap, the QLSSD system 120 may send a message to the clinician system that enables a clinician to select a brightest area of the liver or indicate that liver is not visible. The clinician may also be able to select the brightest spleen area. Based on the selection, the image detector 124 can use directional searching and centroid analysis to re-identify the liver and spleen. In some embodiments, clinicians may be given an option to select the liver and spleen pixels before any of the search process. Thus, the QLSSD system 120 can validate organ detection.

Figure 4:
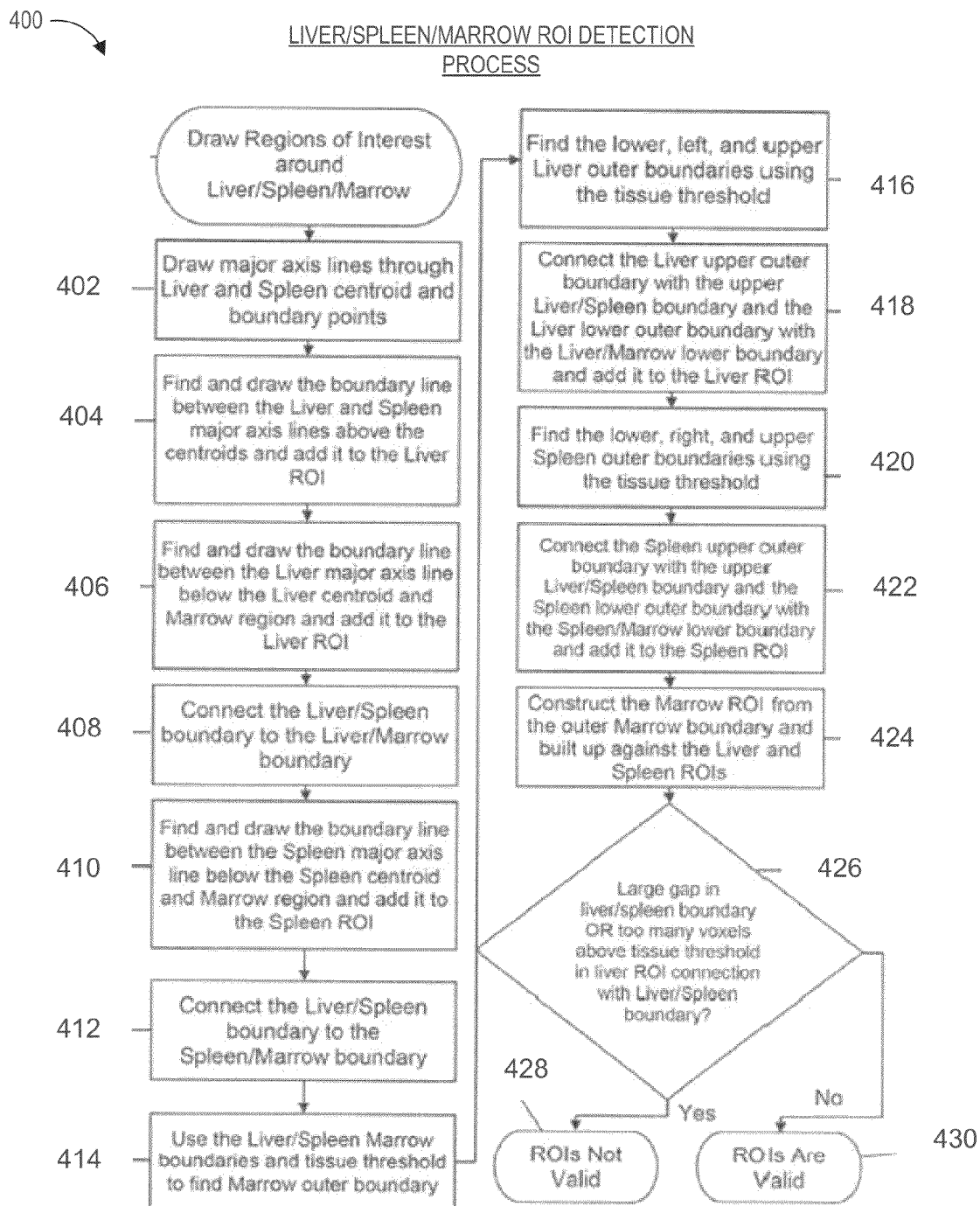
FIG. 4 illustrates an embodiment of a process for identifying liver, spleen, and bone marrow ROI.
Figure 15:
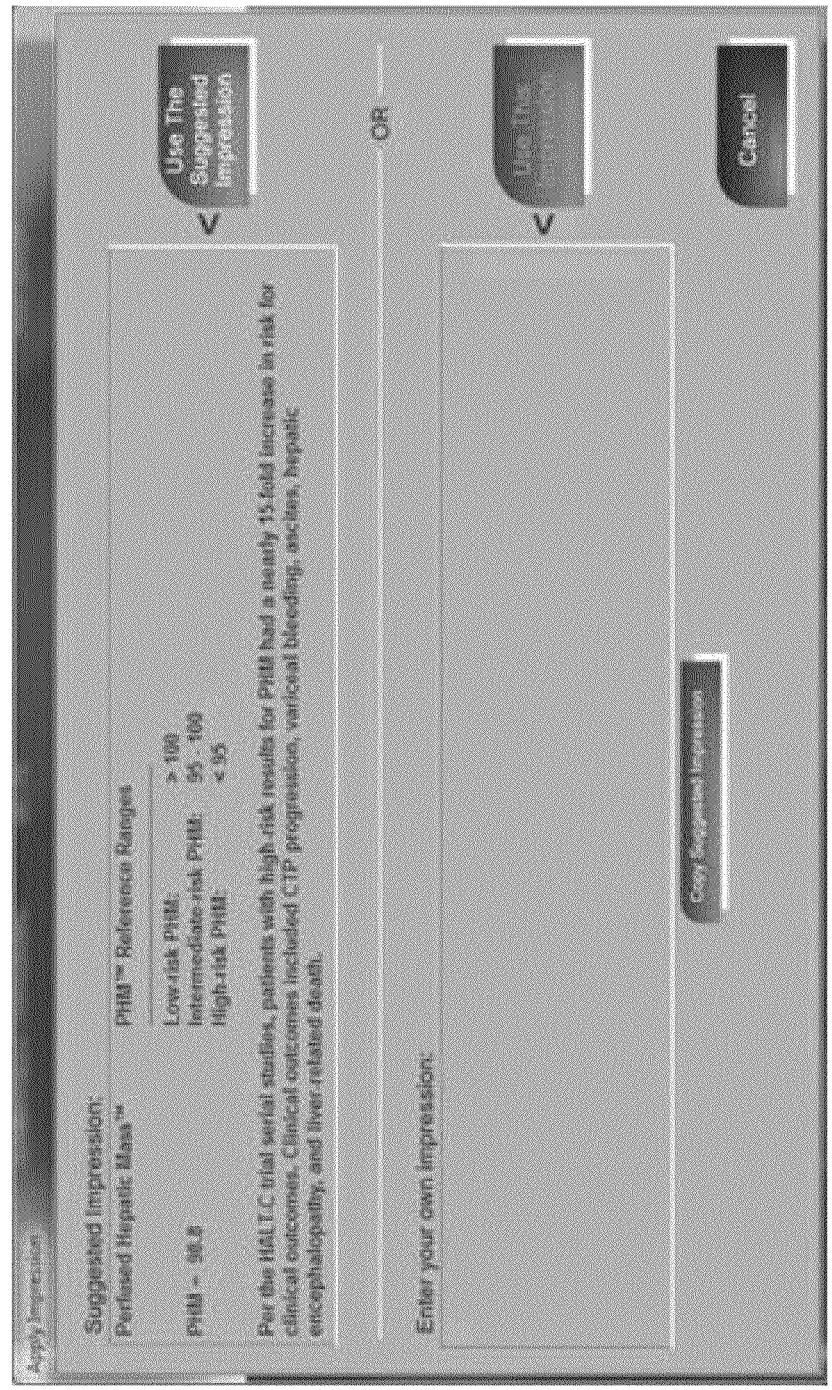
FIG. 15 illustrates an embodiment of a user interface that includes a suggested impression and enables clinicians to enter their own impressions.

If the liver and spleen regions are validated, then at block 330, the image detector 124 can automatically draw ROIs around liver, spleen, and bone marrow as described more in detail with respect to FIG. 4. Once the ROIs are determined, the parameter calculator 126 can calculate parameters corresponding to hepatic function as discussed below. In some embodiments, the process 300 includes the step of preparing and generating a report including impressions at blocks 332-334. The user interface generator 128 can prepare reports based on the calculated parameters and a lookup table. The lookup table may be stored in the data repository 140. The lookup table can store appropriate impressions for different ranges of parameters. An example impression is shown in FIG. 15.

V. Regions of Interest Analysis

FIG. 4 illustrates an example ROI detection process 400 for determining ROIs based on the detected liver and spleen centroids using the process illustrated in FIG. 3. The ROI detection process 400 can be implemented by the system described above. For illustrative purposes, the process 400 will be described as being implemented by components of the computing environment 100 of FIG. 1.

In an embodiment, once the liver and spleen centroids are identified along with boundary points, the image detector 124 can proceed with identifying region of interests to segment liver, spleen and bone marrow. At block 402, the image detector 124 can fit in a geometric shape such an elliptical shape over the liver and spleen based on the respective boundary points and centroid detected by the process 300 discussed above. As an example, the image detector can fit an ellipse based on a least squared error reduction method. In some embodiments, the major axis of the fitted ellipse passes through the centroid of the detected organs.

The image detector 124 can determine a centroid-centroid line connecting the centroid of the liver to the centroid of the spleen at block 404. The image detector 124 can then identify a boundary point along the centroid-centroid line that corresponds to a valley (lowest) in count distribution. The image detector 124 can find additional boundary points north (or above) of the centroid-centroid line using the liver and spleen major axis as the starting points and finding the minimum concentration in between. The image detector 124 can use these boundary points to obtain a demarcation line between the liver and the spleen. An example demarcation line (or liver-spleen boundary line) 610 is illustrated in FIG. 6. One side of the demarcation line can be the liver ROI 602 and the other side of demarcation line can be part of the spleen ROI 606.

At block 406, the image detector 124 can detect a boundary line 612 (see FIG. 6) between the liver and the bone marrow. In an embodiment, the image detector 124 can attempt to calculate centroid of the bone marrow and the liver-marrow boundary line can be calculated as discussed above. But, in some embodiments, the image detector 124 may not be able to identify a bone marrow centroid. In these instances, the image detector 124 can start from a point (below the centroid) on the major axis of the liver ellipse and look for pixels in the direction of bone marrow where the value of count is at a certain liver-marrow number. In one embodiment, the liver-marrow number=threshold (as calculated above)+20% (maximum intensity in liver−threshold). Other variations and percentages can be also be used. Accordingly, the image detector 124 can identify boundary line 612 between liver and bone marrow.

At block 408, the image detector 124 can connect the liver-spleen boundary 610 with the liver marrow boundary 612 as seen in FIG. 6. As discussed above with respect to liver, at block 410, the image detector 124 can identify a spleen-bone marrow boundary line 614 using a spleen-marrow number. In one embodiment, the spleen-marrow number=threshold+20% (maximum intensity in spleen−threshold). At block 412, the image detector 124 can connect the liver-spleen boundary 610 to the spleen-marrow boundary 614 as illustrated in FIG. 6.

At block 414, the image detector 124 can detect outer boundary 616 (see FIG. 6) of the marrow. In an embodiment, the image detector 124 can connect the end point of the liver-marrow boundary to the end point of the spleen-marrow boundary. The image detector 124 can use the tissue threshold to connect the end points. At block 416, the image detector 124 can find the outer boundary 618 of the liver using the tissue threshold and body contour as discussed above. The image detector 124 can connect the outer boundary 618 to the end point of the liver-marrow boundary on the bottom and the end point of the spleen-marrow boundary on the top.

Similarly, at block 420, the image detector 124 can find the outer spleen boundary 620. The image detector 124 can connect the outer spleen boundary 620 to the end point of the liver-spleen boundary on the top and the end point of the spleen-marrow boundary on the bottom at block 422. Accordingly, the image detector can generate liver ROI 602 and the spleen ROI 606 from the calculated boundaries. The image detector can generate the marrow ROI 604 from the liver-marrow, spleen-marrow, and the outer marrow boundaries.

In some embodiments, the image detector 124 can validate the calculated ROIs. For example, the image detector 124 can check whether there is a large gap in liver-spleen boundary or if there are too many voxels above tissue threshold in liver ROI connection with liver/spleen boundary. Based on the validation, the user interface generator 128 can generate a user interface that can enable a clinician to modify the generated ROIs.

The ROIs calculated using the QLSSD system 120 can be robust compared to hand drawn ROIs. For instance, there may be variations in hand drawn ROIs between different clinician. Moreover, it may be cumbersome and time-intensive to hand draw ROIs. Also, the clinicians may not be able to detect counts appropriately from the image as it may depend on the contrast levels of images and may vary between scanners.

VI. Parameters

As discussed above, most of the existing health detection techniques suffer from subjective analysis. There is a lack of an objective analysis that is repeatable (within a small error range) between clinicians and patients. The QLSSD system 120 can abstract parameters from the scanned images to generate objective parameters for evaluating hepatic function. The parameter calculator 126 can use the processed images with detected ROIs to calculate one or more of the following parameters. Other variations in calculation of these parameters are possible as can be understood by a person skilled in the art.

Liver, Spleen, and Bone Marrow Counts

In SPECT images, the counts correspond to detected radiation from the compound. Accordingly, higher counts may indicate higher concentration of the compound in a particular organ. The parameter calculator 124 can use the detected ROIs for liver, spleen, and bone marrow to calculate total counts in each of the respective ROIs from one of the combined transaxial image. For combined frames, the counts can represent volume as the stack of frames may include multiple slices of the patient's body. In some embodiments, a single mid-organ frame is used to compute liver and spleen concentration. Concentration may also be computed by averaging counts in a particular sub-region of the organ from a frame with the highest counts. The image detector can find 3×3 voxel areas in the highest count frame and average the counts to determine a concentration (e.g. counts/minute/voxel). For three dimensional ROIs, the counts may be summed across all frames for respective organ ROIs. The counts can indicate to clinicians how much of the compound is in the liver versus the other organs. As discussed above, for a healthy liver, most of the counts might be found in the liver ROI as compared to other organ ROIs. In some embodiments, bone marrow counts are expressed as a ratio to the number of frames to normalize for number of vertebral bodies covered by the scan. In another embodiment, the number of vertebral bodies is counted and that is used to normalize the bone marrow counts.

Liver and Spleen Length

In an embodiment, the parameter calculator 128 can calculate lengths of detected organs. For example, the parameter calculator 128 can detect length of the liver from an anterior planar image for right lobe from mid-liver dome to the right inferior margin and left love from right dome to inferior left lobe margin.

The parameter calculator 128 can measure the spleen length as the greatest pole to pole length in posterior planar view. In some embodiments, the spleen length is determined from the transverse images. If there is a difference in spleen length by 10% or more between different frames, the clinician may be warned and manual intervention may be required via one of the user interfaces described below.

Liver Spleen Index, Liver Bone Marrow Index (LBI), and Perfused Hepatic Mass (PHM)

In some embodiments, the hepatic function may be understood from distribution ratios using counts obtained from the one or more scanned images. For instance, the liver-spleen index (LSI) can be determined from comparing counts in the liver to the counts in spleen. In an embodiment, the liver-spleen index (LSI) is a function of liver to spleen ratio of total counts corrected for spleen length. The parameter calculator 128 can calculate total count ratio between liver and spleen as a total liver counts divided by total liver plus spleen counts, or $L/(L+S)_t$. In some embodiments, the ratio is reproducible within 1%. The ratio might be affected by spleen size independent of chronic liver disease. A correction might be required for variation in spleen length between patients. In one embodiment, the parameter calculator 128 can correct for the spleen length. The parameter calculator 128 can estimate the $L/(L+S)_t$ ratio expected from the impact of spleen length in patients with normal livers (empirically derived formula from patients with normal livers and varying size spleens). The parameter calculator can then divide the measured $L/(L+S)_t$ ratio by the estimated normal $L/(L+S)_t$ ratio and multiply it by 100 to derive the liver spleen index (LSI).

The distribution of counts between liver and bone marrow may be expressed as the liver-bone marrow index (LBI). In an embodiment, the parameter calculator 128 can calculate LBI as the log of liver count divided by bone marrow count per frame and multiplied by 50 to produce a similar range to LSI.

In some embodiments, the parameter calculator 128 can generate a parameter that is a function of both LSI and LBI. For example, the parameter calculator 128 can calculate the perfused hepatic mass (PHM) parameter by averaging of LBI and LSI, that is: PHM=(LBI+LSI)/2.

Spleen and Liver Volume

The parameter calculator 128 can also calculate liver and spleen volumes. Spleen and liver volumes may be calculated using the total counts in an organ divided by a representative concentration on the cross-sectional frame times the voxel volume. In one embodiment, the parameter calculator 128 can use a single mid-organ frame that is representative for the concentration. The volumes in cc may be expressed as a ratio to the ideal body weight (IBW) in pounds. One skilled in the art can recognize alternate methods of obtaining representative concentrations of the organ of interest, such as, sampling, histogram analysis, whole organ averaging, or single organ slice. Additional example calculations are discussed in "A Novel, Simple Method of Functional Spleen Volume Calculation by Liver-Spleen Scan," by Hoefs et al, The Journal of Nuclear Medicine, Vol. 40, No. 10 (October 1999), incorporated herein by reference in its entirety. In some embodiments, volumes do not rely on precise edge detection and are insensitive to voxel size.

In some embodiments, the liver volume is automatically calculated by performing a search through the scanned images to identify a frame that contains the highest concentration areas of the liver. The image detector can find 3×3 voxel areas in the identified frame and average the counts to determine a concentration (e.g. counts/minute/voxel). The parameter calculator 128 can use the highest average concentration value to calculate the volume of the liver using the following formula and example calculation:

Liver Volume=((Total Liver Counts/Highest Average Liver Concentration)* Voxel Size*0.9562)−66.5.

Total counts liver=8600000 CPM
Representative concentration=860 CPM/voxel
Voxel volume (0.474 cm on a side)=0.474 cubed=0.474*0.474*0.474=0.10650 cc
Raw volume=(8600000/860)×0.1065=1065 cc
Corrected volume=raw volume×correction factor=(1065× 0.9562)−66.5=952 cc The constants in the liver volume formula can be modified based on calibration samples. For example, the calculated volume can be compared to phantom volumes by linear regression analysis. The spleen volume can be calculated using the method discussed above with respect to liver. In an embodiment, each voxel represents a 4×4×4 cubic millimeters. Accordingly, the liver volume can be determined in cubic millimeters.

Normalized Liver and Spleen Volumes

Liver and spleen volumes may depend on the patient's overall size. Thus, in some embodiments, ideal body weight is used to normalize the organ volumes to provide clinically useful parameters. The patient's actual body (e.g. obtained from PACS) may also be used. The parameters can be calculated as follows:

Normalized Liver Volume=Liver Volume/Ideal Body Weight

Normalized Spleen Volume=Spleen Volume/Ideal Body Weight

The formula to calculate IBW may be different for males and females.

Female IBW=100+{height (in inches)−60}×5

Male IBW=106+{height (in inches)−60}×6

Example: if the liver volume is 952 as calculated in the example above, then A Female, 62 inches tall would have an IBW=110 lbs and the Normalized Hepatic volume (corrected for body size)=8.7 cc/lb IBW Estimated Peritoneoscopic Score (estPS)

Peritoneoscopy can provide an indication of the degree of "smoothness" or "granularity" or "nodularity" of the liver. The QLSSD can calculate an Estimated Peritoneoscopic Score (estPS) by combining several parameters. In one embodiment, the estPS is calculated as follows:

estPS1=4.342−2.008RR−0.0206PHM+18.15/RL where RL is the right lobe length in cm, and RR is the redistribution ratio calculated as:

(RR)=[(Lp/Sp/2.5)+(Lp/BMp/17.5)]/2

Here Lp, Sp and BMp are pixel counts from the posterior planar view for the liver, spleen and bone marrow respectively.

The Peritoneoscopic assessment of the liver can be a better indicator than histologic fibrosis measurements since sampling errors may be avoided. Thus, the estPS from QLSSD can provide a good estimate of hepatic fibrosic stage as measured by histology with almost no sampling error.

Staging

The parameter calculator 126 can classify severity of liver disease by comparing one of the calculated parameters with expected ranges. In one embodiment, patients are staged using the PHM parameter as follows:

PHM≥100; normal hepatic function (low risk)
95≤PHM<100: mildly reduced hepatic function (intermediate risk)
PHM<95: reduced hepatic function (high risk)

In another embodiment, high risk patients are further classified as moderately reduced hepatic function if the PHM>70 or severely reduced hepatic function if PHM<70. Other indicators including colors may also be used for staging. these ranges may vary in other embodiments, or may have more or fewer ranges (e.g. a threshold may be used to determine if the patient's liver is healthy or not).

Hepatic Activity Index

There may be a close correlation between LSI and LBI. A linear regression equation drawn in a large group of patients can define this relationship. In an embodiment, the LSI can be used in this equation to determine an estimated LBI. The estimated LBI may be subtracted from the Measured LBI and this difference can be divided by the LSI to get the HAI. The HAI of less than a−0.10 can indicate a significant departure from the usual relationship and indicates a more rapidly progressive liver disease such as alcoholic hepatitis.

In some embodiments, the formula for calculating HAI is: If LSI>0.0

$$HAI=(LBIt-((LSI*0.665)+43.0))/LSI$$

Otherwise $$HAI=0$$

VII. 3D Processing

Figure 7:
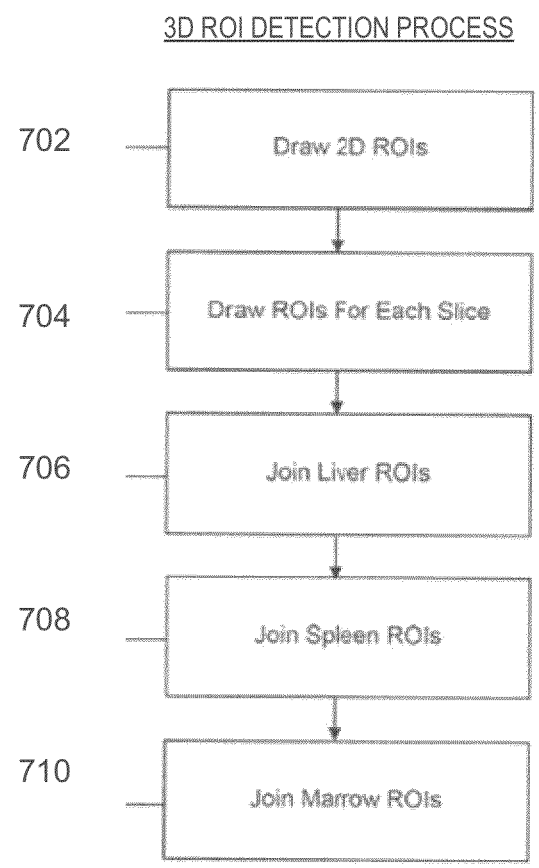
FIG. 7 illustrates an embodiment of a process to detect three dimensional ROIs.

In some of the embodiments discussed above, the frames corresponding to slices across the patient's body can be analyzed as combined frame (e.g. STI, MITI, etc.). In the alternative, the frames can be processed individually to detect three dimensional profile of organs. FIG. 7 illustrates a process for detecting ROIs in three dimensions. The 3D ROI detection process 700 can be implemented by the system described above. For illustrative purposes, the process 700 will be described as being implemented by components of the computing environment 100 of FIG. 1.

At block 702, the image detector 124 can detect 2D ROIs of liver, spleen, and bone marrow as discussed above with respect to FIGS. 3 and 4. The image detector 124 can continue detecting ROIs for each frame. Some frames may have low signal content as the organs begin to taper off. The image detector 124 can store the ROIs from each of the frames for liver, spleen, and bone marrow. At block 706, the image detector 124 can combine the stored liver ROIs using morphological features to form a 3D liver volume. Similarly, the image detector 124 can generate 3D spleen volume at block 708 and a 3D bone marrow volume at block 710. In some embodiment, the image detector 124 can use edge following to connect ROIs between frames. The parameter calculator 126 can calculate liver function parameters and liver disease stages from the 3D ROIs using the formulas as discussed above with respect to 2D frame.

In some embodiments, the image detector 124 can generate 3D ROIs using directional searching and centroid in three dimension instead of combining the results of 2D analysis for individual frames. In three dimensions, the image detector 124 can rotate direction vector of search before conducting iterative directional searching and centroid analysis. In another embodiment, the image detector 124 can use transform processes to map 3D volumes (such as ellipsoids) into points in the transform space. For instance, the liver, spleen, and marrow may be modeled as ellipsoids (or union of ellipsoids) to use the transform techniques.

The 3D capability may also allow calculation of fibrosis directly. In some embodiments, the functional ratios can overlap because there might be overlap between liver, bone marrow and spleen. Separating the frames before analyzing can reduce effects of overlap.

The image detector 124 may also use data from CT or MRI scan. The CT and MRI scan include information relating to outline of organs. The image detector 124 can use the outline to map data from SPECT scan on to a CT or MRI scan. Based on the mapping, the image detector 124 can detect ROIs from the SPECT scan.

VIII. Total Count Ratio (TCR)

The SPECT reconstruction may have a limited range of slices that includes the entire organ being evaluated. Each slice may be the width of the voxel (or pixel). A threshold can be designated as to the surface voxel for inclusion of a surface voxel as a percent of the maximal voxel concentration in the liver. As the liver becomes more diseased, fewer of the surface voxels might have greater than 50% of the maximal voxel concentration due to the presence of fibrosis. Thus, the volume of the included voxels may be smaller as the liver becomes more diseased (and total counts in this 3-D ROI decreases). The included volume in patients with chronic liver disease has fewer counts compared to the total counts (TCR) compared to a similar procedure on a normal liver. The total counts ratio can be calculated from summarized transaxial image.

The image detector 124 can determine ROI around the organs as discussed above. Based on the ROIs, the total counts (TC) for each of the organs may be calculated by the parameter calculator 126. The parameter calculator 128 can select a threshold. In an embodiment, the threshold is 50% of the maximal voxel concentration). The parameter calculator 126 can apply the threshold to each slice within the above ROI, therefore picking the surface voxel to be used on each slice. The image detector 124 can take the surface voxels selected from each slice to draw a 3-D image for the whole organ. The parameter calculator 126 can calculate the counts within the generated 3-D image. These counts can represent the threshold counts. The parameter calculator 126 can calculate the total count ratio (TCR), where TCR=threshold count/total count (TC) for each organ. Accordingly, TCR can be calculate for the organs and included in reports.

IX. Predicting Post-Op Surgery 3D imaging can enable pre-surgery estimates of the loss of hepatic function after surgery for hepatocellular carcinoma (HCC) and other hepatic masses. The expected anatomic loss from surgery can be overlaid with the 3D ROIs and the loss of function calculated. These factors may be used in the output impressions to stage the liver disease, estimate the risk of complications and for prognosis. In patients with hepatic cancer and limited hepatic reserve, the liver health parameters may be used to estimate the loss of function at surgery to determine surgical risk.

Figure 8:
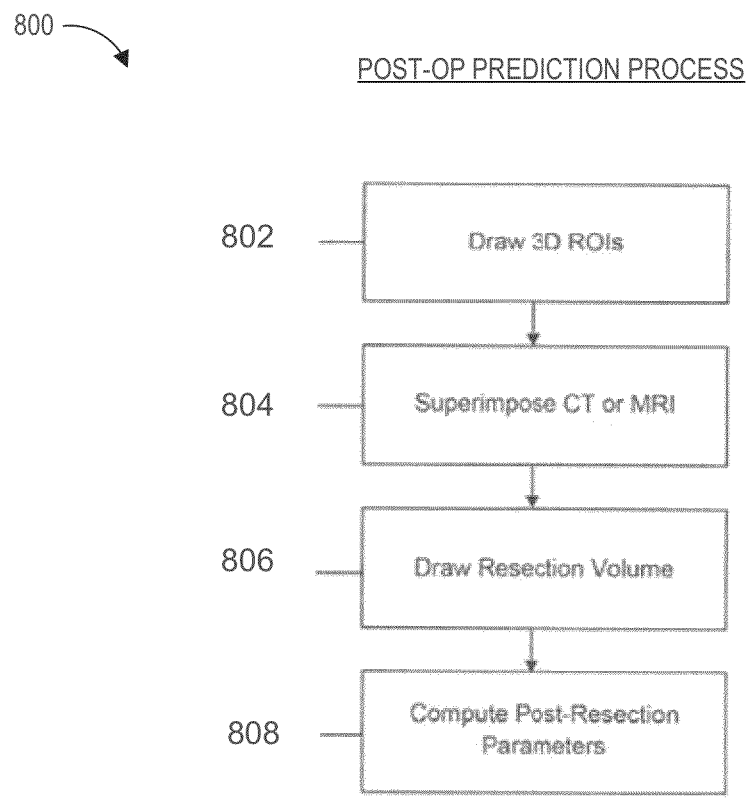
FIG. 8 illustrates an embodiment of a process for predicting post-surgery liver health.

FIG. 8 illustrates an embodiment of a process 800 for estimating post-resection parameters. The post-resection parameter calculation process 800 can be implemented by any of the systems described above. For illustrative purposes, the process 800 will be described as being implemented by components of the computing environment 100 of FIG. 1. At block 802, the image detector 124 can determine 3D ROIs of the liver, spleen, and bone marrow as discussed above. At block 804, the image retriever module 122 can access CT or MRI images including the liver. The image detector 124 can superimpose the CT or MRI image on the 3D ROIs using, for example, image registration techniques.

In some embodiments, superimposition may be performed using built-in capabilities of hybrid SPECT/CT scanners. At block 806, the user interface module 128 can generate a user interface that can allow clinicians to select or draw resection volume on the superimposed image. In an embodiment, the resection volume is automatically drawn based on importing parameters from surgical planning system. In some embodiments, the QLSSD system 120 can display a suggested resection volume. The suggested resection volume may be based on the differences between the SPECT liver volume and the CT or MRI liver volume. As an example, portions of the liver that contain hepatocellular carcinoma (HCC) will show up in the CT or MRI images but not in the SPECT images. At block 808, the parameter calculator can ignore the area that is part of the planned resection volume to calculate post-resection parameters. Accordingly, the process 800 can enable clinicians to determine liver health post operation and determine whether more or less of the liver should be removed. Also, the clinicians can assess risk of surgery by reviewing the post-resection parameters.

X. User Interfaces

The example graphical user interfaces shown in FIGS. 9 to 18 may be generated by the QLSSD system 120, the QLSSD system plugins, or a combination of both. For illustration purposes, these user interfaces are shown primarily in application interfaces, although it should be understood that these user interfaces can be generated with web browsers (including mobile apps) other than application interfaces. Further, example user interface controls (active links) are shown, including buttons, status bars, hyperlinks or links, and the like. Any of the user interface controls shown can be replaced with other user interface controls, including but not limited to radio buttons, check boxes, text boxes, select boxes or drop-down boxes, combinations of the same, and the like.

Figure 9:
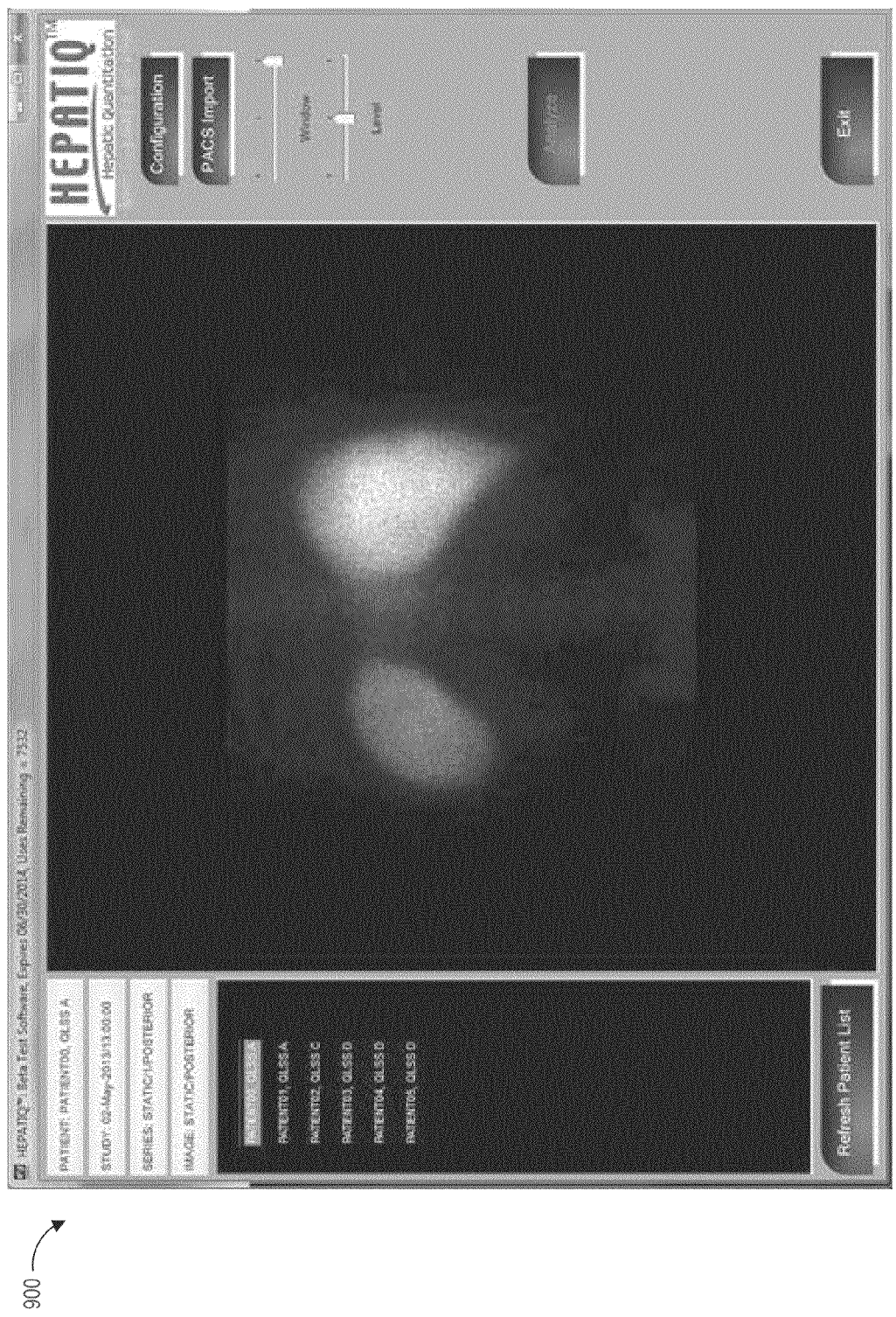
FIG. 9 illustrates an embodiment of a user interface that can enable clinicians to generate health parameters corresponding to liver's healthiness.

FIG. 9 illustrates an embodiment of a user interface 900 generated by the user interface module 128 that can enable clinicians to access functionality of the QLSSD system 120. For example, clinicians can import scanned images for a patient from PACS and view the scanned images in the user interface. The user interface also include active links to change contrast and brightness of the scanned image. Clinicians can further run automated analysis on the scanned images by selecting an active link. The user interface 900 can enable clinicians to navigate a DICOM hierarchy for the selected image (patient, study, series, and image). The navigation button and list can facilitate moving from one image to another, to refresh patient list, etc. Moreover, images can be imported from PACS such as SPECT transverse images and/or static posterior planar images. In some embodiments, image are imported automatically from PACS. The clinician can select an image or a set of images for analysis by the QLSSD system as discussed above.

Figure 10:
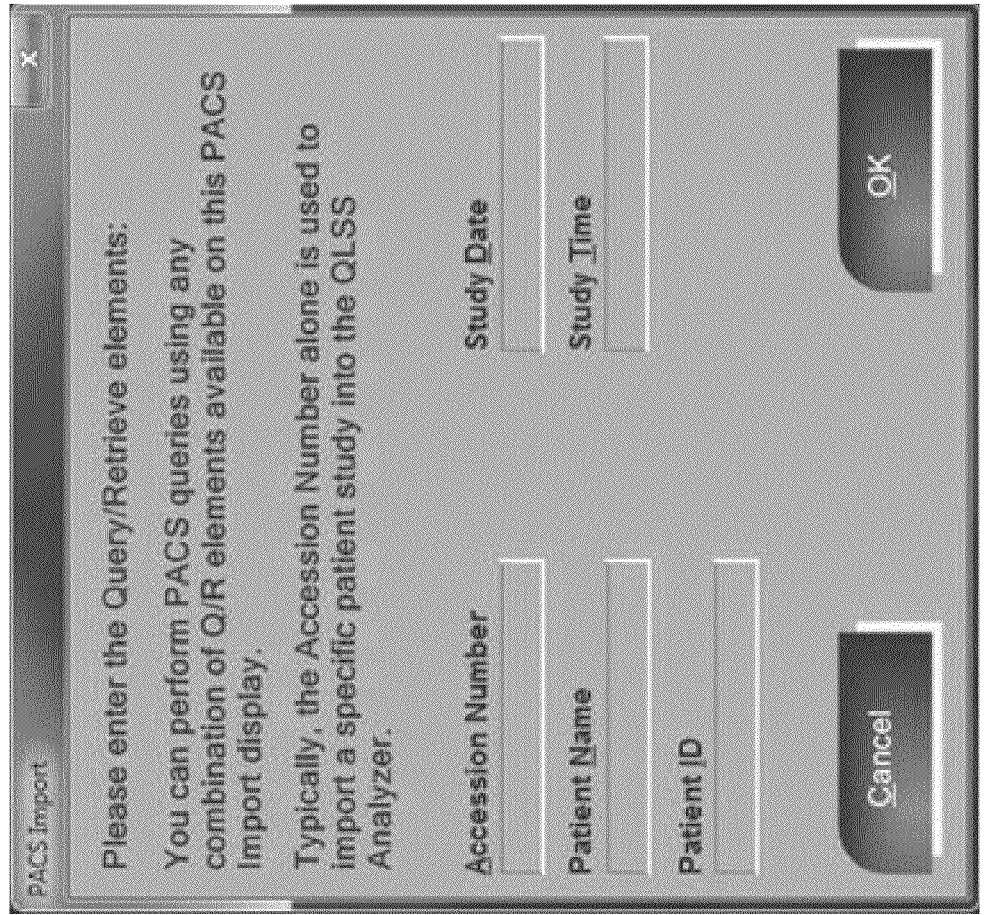
FIG. 10 illustrates an embodiment of a PACS import user interface.

FIG. 10 illustrates an embodiment of a user interface 1000 generated by the user interface module 128 that can enable communications with the PACS system 102. For example, the clinician can run queries to access data corresponding to a particular patient. Based on the selected query, the QLSSD system 120 can communicate with PACS and retrieve the requested data.

Figure 11:
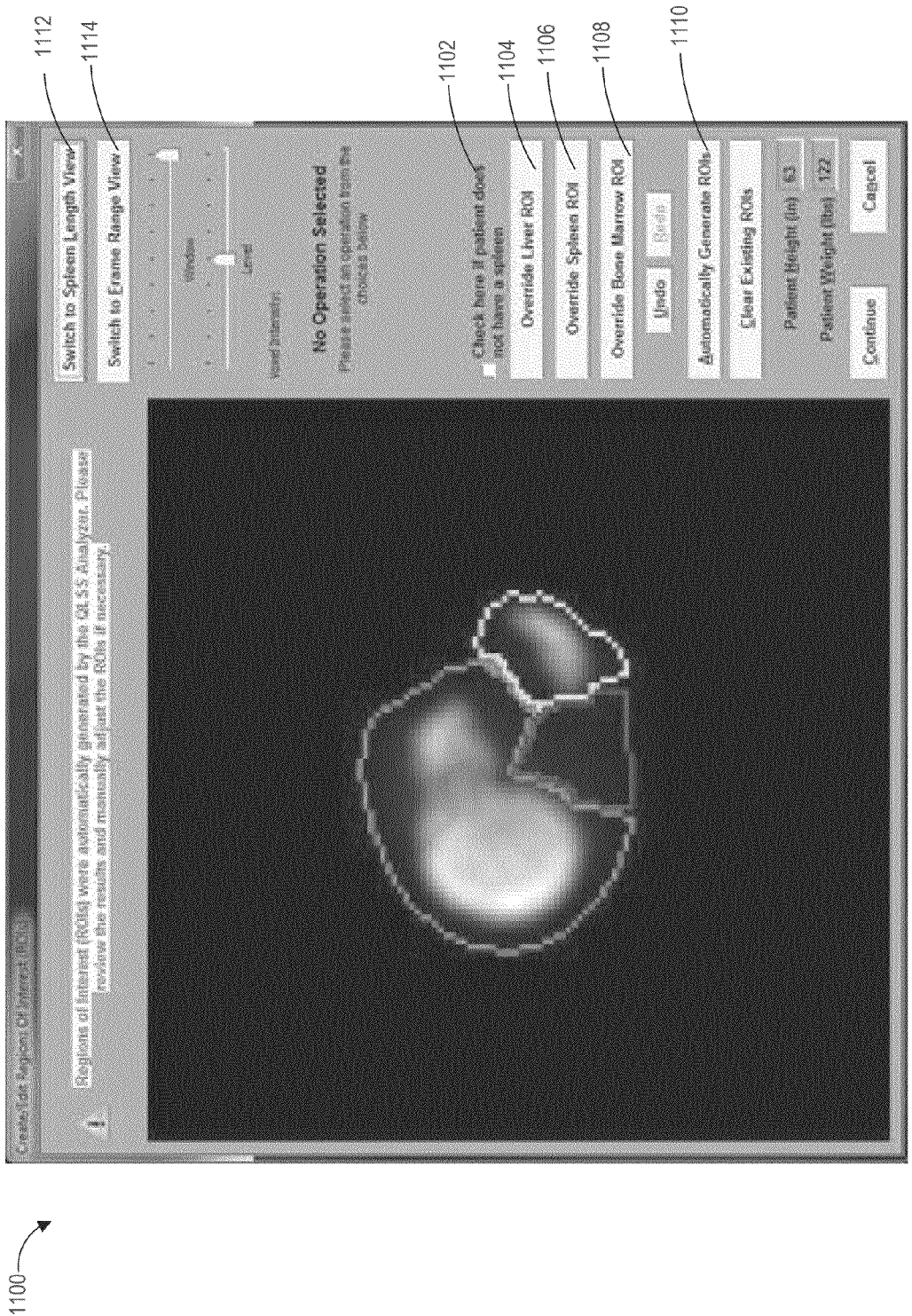
FIG. 11 illustrates an embodiment of a user interface that allows clinician to review and modify automatically generated ROIs.
Figure 12:
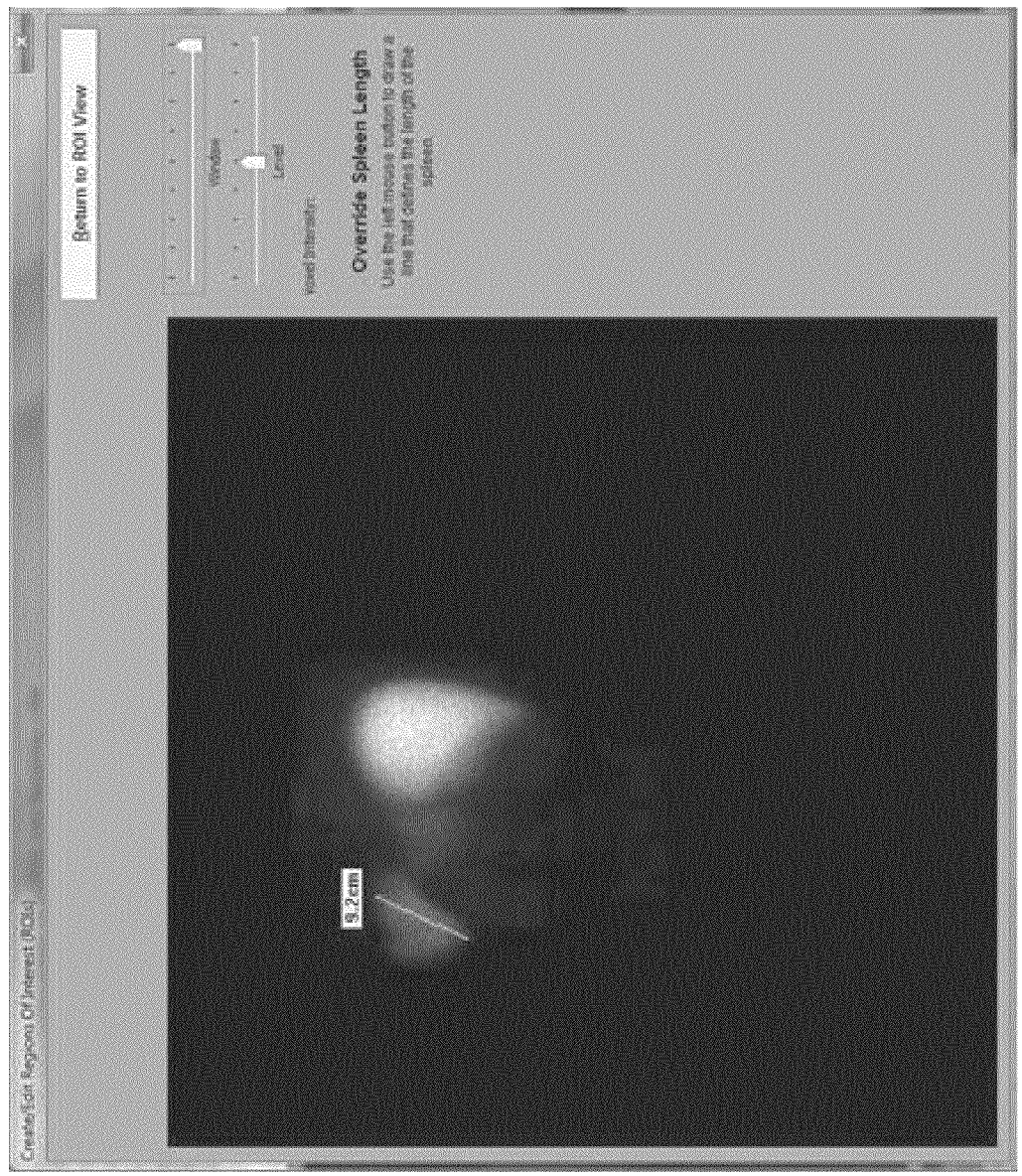
FIG. 12 illustrates an embodiment of a user interface showing length of a patient's spleen.
Figure 13:
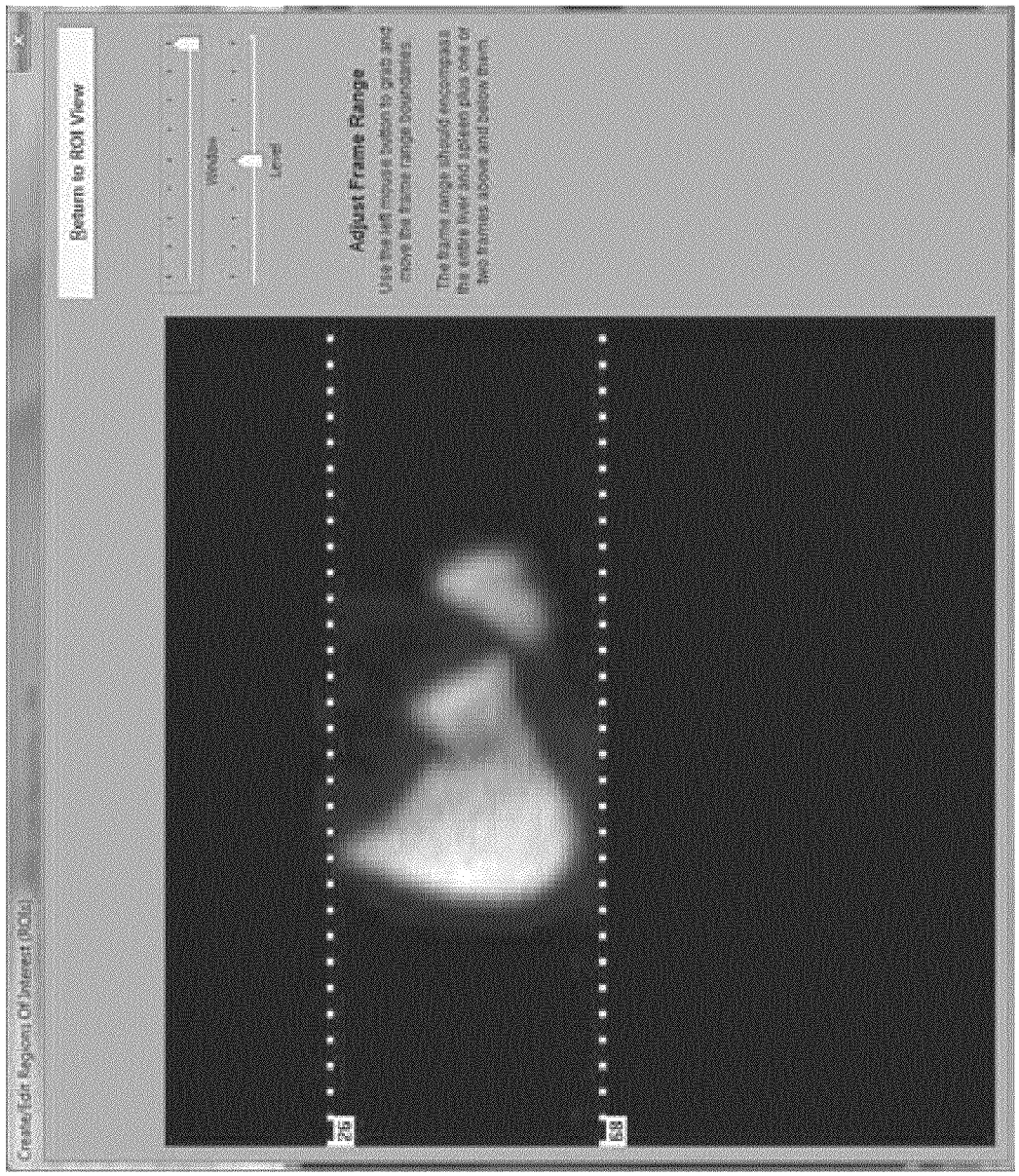
FIG. 13 illustrates an embodiment of a user interface that can enable clinicians to adjust frame range.

FIG. 11 illustrates an embodiment of a user interface 1100 that can be generated by the user interface module 128 in response to the detected regions of interest corresponding to organs. The illustrated embodiment of the user interface 1100 shows liver, spleen, and bone marrow ROIs. The user interface 1100 can include an active link 1102 for selecting whether the patient has his or her spleen removed. For patients with no spleen, the ROI detection may need to be repeated by selecting active link 1110 or manually determined from clinicians using active links 1104, 1006, and 1108. The user interface 1100 also includes link 1112 to select spleen length view as shown in FIG. 12 and link 1114 to select frame range view as shown in FIG. 13. The spleen length user interface 1200 can enable clinicians to visually confirm the length of the spleen as calculated by the QLSSD system 120. The spleen length user interface 1200 can also enables functionality for the clinician to override calculated spleen length. In the illustrated embodiment, the spleen length is 9.2 cm and scanned image is showing a posterior view of the liver and the spleen. FIG. 13 illustrates an embodiment of a user interface 1300 that can enable clinicians to select the frame range. In some instances, the image detection module 124 can identify a larger portion of the bone marrow and may include pelvis region. The clinicians 1300 can select the frame range to guide the image detector module 124 to more accurately calculate the ROIs. The user interface 1300 can enable clinicians to visually confirm that the range of frames detected by QLSSD system 120 encompasses the entire liver and spleen.

Figure 14:
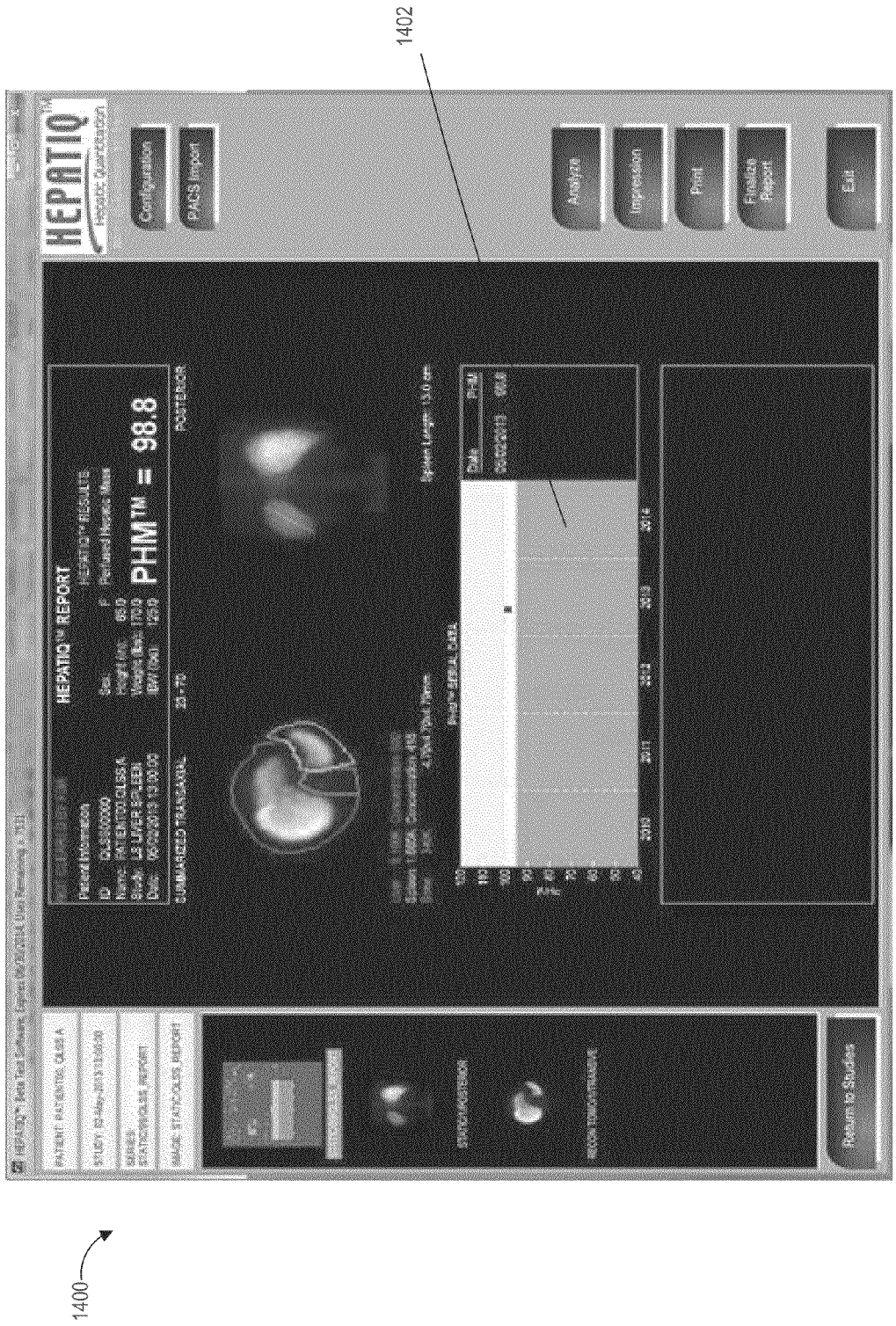
FIG. 14 illustrates an embodiment of a user interface including a report with the PHM parameter.

FIG. 14 illustrates an embodiment of a user interface 1400 that includes a report generated by the QLSSD system 120. The user interface module 128 can generate a report in response to receiving a command from a clinician. The illustrated report includes calculation of a PHM parameter for the patient. The report can also include additional details from the patient, such as sex, height, weight, date of the study. In some embodiments, the report can include a trend graph 1402 plotting a parameter over time. In the illustrated embodiment, the trend graph includes PHM over time.

FIG. 15 illustrates an embodiment of a user interface 1500 that enables clinicians to write their impressions for a patient based on the calculated parameter. In some embodiments, the user interface 1500 includes automatically generated impressions that can be used by clinicians. As discussed above, the impressions may be generated by the QLSSD system from lookup tables based on the calculated parameters. The clinician has the option of using the suggested impression from the QLSSD system 120.

Figure 16:
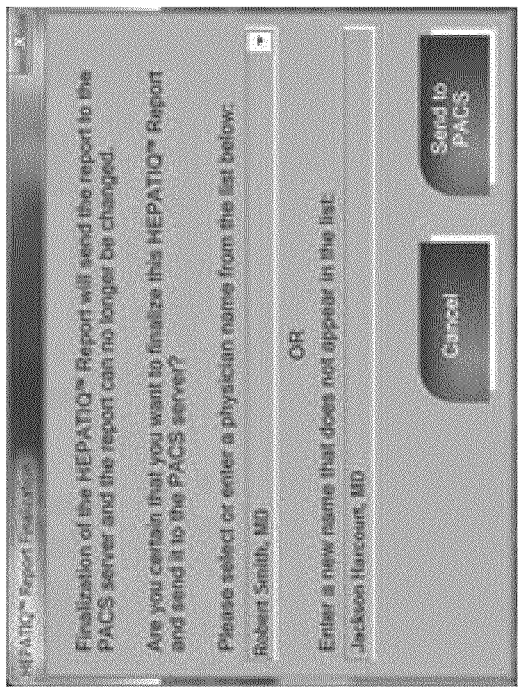
FIG. 16 illustrates an embodiment of a user interface that enables sending a report to PACS.

FIG. 16 illustrates an embodiment of a user interface 1600 that enables clinicians to communicate with PACS. In the illustrated embodiment, the clinicians can use the interface 1600 to send reports for storage in PACS. The reports can be automatically associated with the patient and the doctor.

Figure 17:
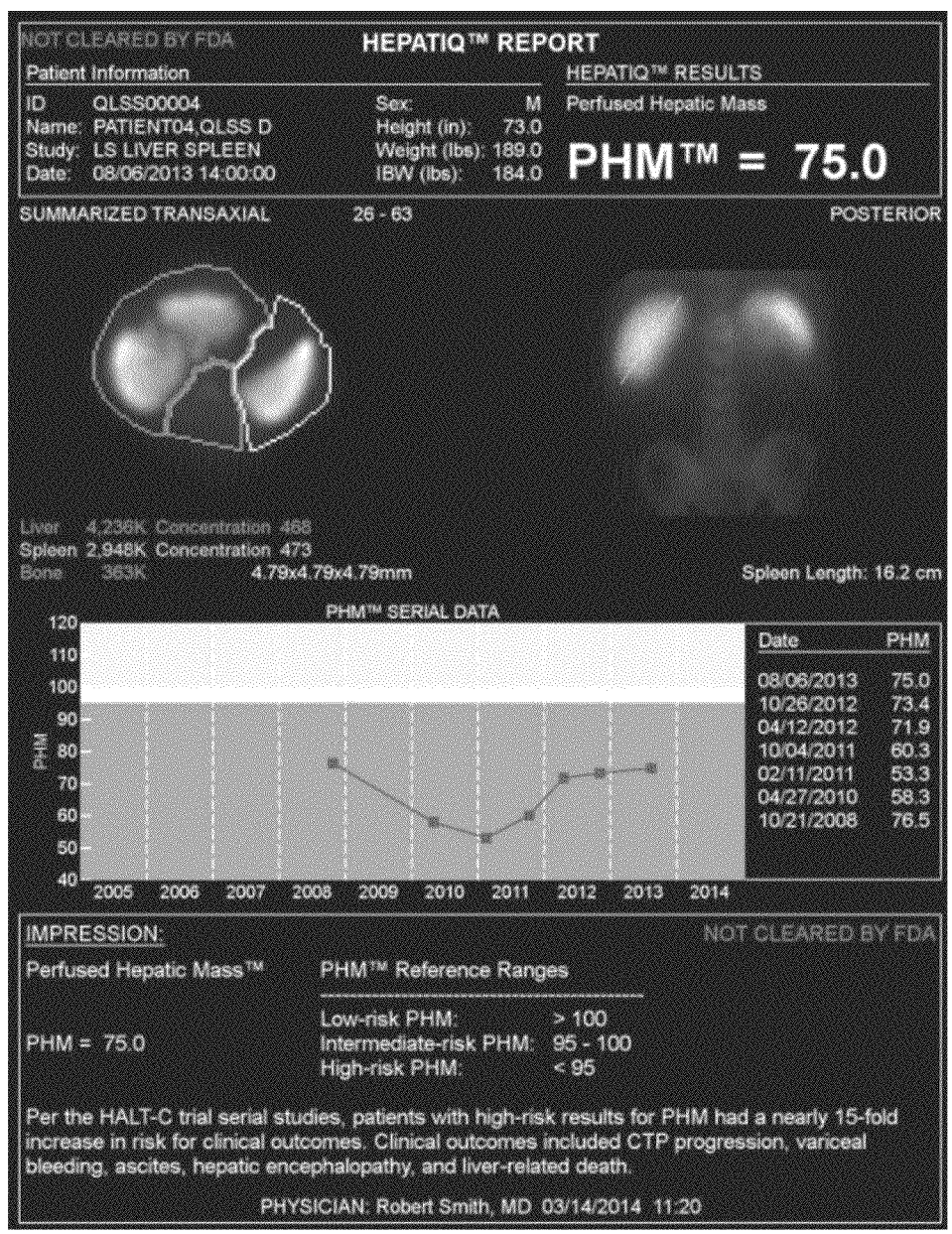
FIG. 17 illustrates an embodiment of a user interface including a report showing a trend in PHM parameter over time.

FIG. 17 illustrates an embodiment of a reporting user interface 1700 that includes a generated report for a patient. The report includes calculated parameters, for example, PHM and a trend in patient's PHM over the years. A clinician can review the trend and identify whether the patient is improving or getting worse. In addition, the clinicians can identify effects of a particular treatment. In some embodiments, the trend can include future prediction based on resection parameters as discussed above. The report can also include impression selected by the clinician or automatically generated by the QLSSD system 120. In some embodiments, the report can illustrate SPECT scans overlaid with detected ROIs.

In one embodiment, the report includes on the left side images from which the raw data were derived: a base image (anterior/posterior), summarized transaxial images, single transaxial slice and distributions of total and planar counts. The sections on the right side have panels for demographics, LSI, LBI and PHM; a panel for volumes by 4 methods (the circled is the one we use); a panel for total counts; 2 panels for posterior planar counts; 2 panels for representative concentrations from the single slice—one for liver and one for spleen; and liver and spleen lengths.

Figure 18:
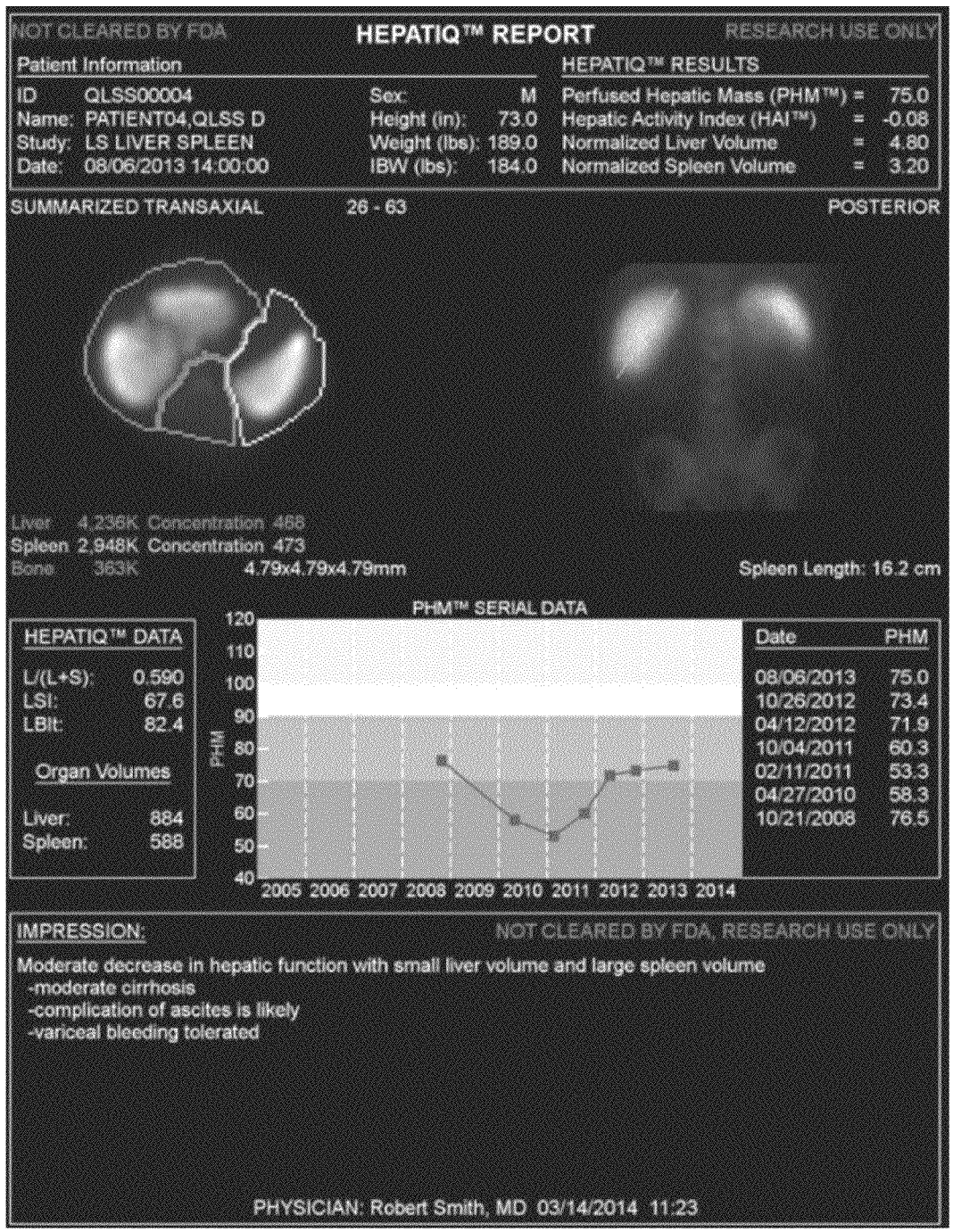
FIG. 18 illustrates an embodiment of a user interface including an example report showing liver health parameters.

FIG. 18 illustrates another embodiment of a reporting user interface 1800 that includes a generated report for a patient. Compared to the report illustrated in FIG. 17, the user interface 1800 includes additional parameters for clinicians.

XI. Terminology

A number of computing systems have been described throughout this disclosure. The descriptions of these systems are not intended to limit the teachings or applicability of this disclosure. For example, the clinician systems and described herein can generally include any computing device(s), such as desktops, laptops, video game platforms, television set-top boxes, televisions (e.g., internet TVs), computerized appliances, and wireless mobile devices (e.g. smart phones, PDAs, tablets, or the like), to name a few. Further, it is possible for the clinician systems described herein to be different types of devices, to include different applications, or to otherwise be configured differently. In addition, the user systems described herein can include any type of operating system ("OS"). For example, the mobile computing systems described herein can implement an Android™ OS, a Windows® OS, a Mac® OS, a Linux or Unix-based OS, or the like.

Further, the processing of the various components of the illustrated systems can be distributed across multiple machines, networks, and other computing resources. In addition, two or more components of a system can be combined into fewer components. For example, the various systems illustrated can be distributed across multiple computing systems, or combined into a single computing system. Further, various components of the illustrated systems can be implemented in one or more virtual machines, rather than in dedicated computer hardware systems. Likewise, the data repositories shown can represent physical and/or logical data storage, including, for example, storage area networks or other distributed storage systems. Moreover, in some embodiments the connections between the components shown represent possible paths of data flow, rather than actual connections between hardware. While some examples of possible connections are shown, any of the subset of the components shown can communicate with any other subset of components in various implementations.

Depending on the embodiment, certain acts, events, or functions of any of the algorithms, methods, or processes described herein can be performed in a different sequence, can be added, merged, or left out altogether (e.g., not all described acts or events are necessary for the practice of the algorithms). Moreover, in certain embodiments, acts or events can be performed concurrently, e.g., through multi-threaded processing, interrupt processing, or multiple processors or processor cores or on other parallel architectures, rather than sequentially.

Each of the various illustrated systems may be implemented as a computing system that is programmed or configured to perform the various functions described herein. The computing system may include multiple distinct computers or computing devices (e.g., physical servers, workstations, storage arrays, etc.) that communicate and interoperate over a network to perform the described functions. Each such computing device typically includes a processor (or multiple processors) that executes program instructions or modules stored in a memory or other non-transitory computer-readable storage medium. The various functions disclosed herein may be embodied in such program instructions, although some or all of the disclosed functions may alternatively be implemented in application-specific circuitry (e.g., ASICs or FPGAs) of the computer system. Where the computing system includes multiple computing devices, these devices may, but need not, be co-located. The results of the disclosed methods and tasks may be persistently stored by transforming physical storage devices, such as solid state memory chips and/or magnetic disks, into a different state. Each process described may be implemented by one or more computing devices, such as one or more physical servers programmed with associated server code.

Conditional language used herein, such as, among others, "can," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. In addition, the articles "a" and "an" are to be construed to mean "one or more" or "at least one" unless specified otherwise.

Conjunctive language such as the phrase "at least one of X, Y and Z," unless specifically stated otherwise, is otherwise understood with the context as used in general to convey that an item, term, etc. may be either X, Y or Z. Thus, such conjunctive language is not generally intended to imply that certain embodiments require at least one of X, at least one of Y and at least one of Z to each be present.

While the above detailed description has shown, described, and pointed out novel features as applied to various embodiments, it will be understood that various omissions, substitutions, and changes in the form and details of the devices or algorithms illustrated can be made without departing from the spirit of the disclosure. Thus, nothing in the foregoing description is intended to imply that any particular feature, characteristic, step, module, or block is necessary or indispensable. As will be recognized, the processes described herein can be embodied within a form that does not provide all of the features and benefits set forth herein, as some features can be used or practiced separately from others. The scope of protection is defined by the appended claims rather than by the foregoing description.

What is claimed is:

1. A system for detecting a liver health parameter of a patient, the system comprising:
 a single photon emission computed tomography (SPECT) scanner configured to obtain image data of organs of the living patient, including a liver and a spleen of the patient, the SPECT scanner configured to obtain the image data by at least detecting radiation counts responsive to administration of a radioactive compound to the patient; and
 a memory device comprising an image detection module and a parameter calculator stored thereon as computer-executable instructions;
 a hardware processor configured to implement the image detection module by executing the computer-executable instructions to at least:
  access the image data output by the scanner,
  determine a plurality of first boundary points of a first anatomical feature corresponding to the liver of the patient based on a first threshold pixel intensity value;
  determine a first centroid of the first anatomical feature corresponding to the liver based in part on the plurality of first boundary points;
  determine a second centroid of the first anatomical feature corresponding to the liver based in part on the first centroid;

determine a plurality of second boundary points of a second anatomical feature corresponding to the spleen of the patient based on a second threshold pixel intensity value;

determine a third centroid of the second anatomical feature corresponding to the spleen based in part on the plurality of second boundary points;

determine a fourth centroid of the second anatomical feature based in part on the third centroid;

programmatically identify a first region of interest corresponding to the liver of the patient from the image data based in part on the second centroid of the first anatomical feature corresponding to the liver and the fourth centroid of the second anatomical feature corresponding to the spleen, the first region of interest comprising a bounded region around the liver of the patient and being indicative of a size of the liver, wherein the size of the liver is correlated with a health condition of the liver, such that the size of the first region of interest is indicative at least in part of the health condition of the liver;

programmatically identify a second region of interest corresponding to a spleen of the patient from the image data based in part on said identification of the first region of interest;

programmatically identify a third region of interest corresponding to a marrow of the patient from the image data based in part on said identification of the first region of interest corresponding to the liver and the second region of interest corresponding to the spleen; and the hardware processor further configured to implement the parameter calculator by executing the computer-executable instructions to at least:

programmatically determine a first attribute associated with the first region of interest, programmatically determine a second attribute associated with the second region of interest;

calculate a first parameter indicative of the health condition of the liver of the patient based at least in part on the first attribute associated with the first region of interest and the second attribute associated with the second region of interest; and output, in a computer-generated graphical user interface, an indication of the first parameter for presentation to a clinician, enabling the clinician to make a clinical care decision for the patient;

a visual representation of the first region of interest corresponding to the liver of the patient;

a visual representation of the second region of interest corresponding to the spleen of the patient; and a visual representation of the third region of interest corresponding to the marrow of the patient.

2. The system of claim 1, wherein the first parameter comprises perfused hepatic mass.

3. The system of claim 1, wherein the first attribute comprises a representation of radiation counts in the first region of interest.

4. The system of claim 1, wherein the image detection module is further configured to compare a geometric property of the first region of interest relative to the second region of interest.

5. The system of claim 1, wherein the memory further comprising a user interface module comprising additional instructions configured to generate and output a second user interface, the second user interface configured to provide functionality for the clinician to input a command to modify the first region of interest.

6. The system of claim 1, wherein the image detection module is configured to combine a plurality of frames from the image data, said frames corresponding to planes transverse to the patient's body.

7. The system of claim 1, wherein the image data comprises a plurality of frames.

8. The system of claim 7, wherein the image detector module is further configured to programmatically detect the first region of interest from a first frame and programmatically detect the second region of interest from a second frame, wherein said first frame corresponds to a different plane with respect to the patient's body than the second frame.

9. A method for detecting a liver health parameter of a patient, the method comprising:

under control of hardware processor, receiving image data from a single photon emission computed tomography (SPECT) scanner, said image data comprising a representation of detected radiation counts corresponding to one or more organs of the patient.

accessing the received image data outputted by the SPECT scanner;

determining a plurality of first boundary points of a first anatomical feature corresponding to the liver of the patient based on a first threshold pixel intensity value;

determining a first centroid of the first anatomical feature corresponding to the liver based in part on the plurality of first boundary points;

determining a second centroid of the first anatomical feature corresponding to the liver based in part on the first centroid;

determining a plurality of second boundary points of a second anatomical feature corresponding to a spleen of the patient based on a second threshold pixel intensity value;

determining a third centroid of the second anatomical feature corresponding to the spleen based in part on the plurality of second boundary points;

determining a fourth centroid of the second anatomical feature based in part on the third centroid;

programmatically identifying a first region of interest corresponding to the liver of the patient from the image data based in part on the second centroid of the first anatomical feature corresponding to the liver and the fourth centroid of the second anatomical feature corresponding to the spleen;

programmatically identifying a second region of interest corresponding to the spleen of the patient from the image data based in part on said identification of the first region of interest;

programmatically identify a third region of interest corresponding to a marrow of the patient from the image data based in part on said identification of the first region of interest corresponding to the liver and the second region of interest corresponding to the spleen;

determining a first parameter indicative of health of the patient based at least in part on a first attribute of the first region of interest corresponding to the liver and also based on a second attribute of the second region of interest corresponding to the spleen;

generating a first user interface configured to display:

a visual representation of the first region of interest corresponding to the liver of the patient a visual representation of the second region of interest corresponding to the spleen of the patient; and a visual representation of the third region of interest corresponding to the marrow of the patient; and programmatically generating an output responsive to the first parameter for presentation to a clinician, wherein the output comprises one or more of a value of the first parameter and a health report associated with the first parameter.

10. The method of claim 9, wherein the first parameter comprises perfused hepatic mass.

11. The method of claim 9, wherein the first attribute comprises a representation of radiation counts in the first region of interest.

12. The method of claim 9, further comprising comparing a geometric property of the first region of interest relative to the second region of interest.

13. A system for detecting a liver health parameter of a patient, the system comprising:

a hardware processor configured to:
receive image data from a single photon emission computed (SPECT) scanner, said image data comprising a representation of detected radiation counts corresponding to one or more organs of the patient;
accessing the received image data outputted by the SPECT scanner;
determine a plurality of first boundary points corresponding to the liver of the patient based on a first threshold pixel intensity value;
determine a first centroid of the plurality of first boundary points;
determine a second centroid of the plurality of first boundary points based at least in part on the first centroid;
determine a plurality of second boundary points corresponding to a spleen of the patient based on a second threshold pixel intensity value;
determine a third centroid of the plurality of second boundary points;
determine a fourth centroid of the plurality of second boundary points based at least in part on the third centroid;
apply image processing techniques to detect a first region of interest corresponding to the liver based at least in part on the second and the fourth centroid;
apply image processing techniques to detect a second region of interest corresponding to the spleen based at least in part on said identification of the first region of interest;
apply image processing techniques to detect a third region of interest corresponding to a marrow of the patient based on the detected first and second regions of interest
determine a parameter corresponding to health of the liver based at least in part of the first region of interest and also based on the second region of interest;
generate a first user interface comprising:
a graphical indication of the parameter;
a visual representation of the first region of interest corresponding to the liver;
a visual representation of the second region of interest corresponding to the spleen; and
a visual representation of the third region of interest corresponding to the marrow; and
a display configured to render the first user interface.

14. The system of claim 13, wherein the parameter comprises one of a liver volume, a spleen volume, a perfused hepatic mass, a total count ratio, a staging indicator, an estimated peritoneoscopic score, a normalized liver volume, a normalized spleen volume, a highest average concentration, liver counts, a liver spleen index, a liver bone marrow index, a liver length, a spleen length, spleen counts, bone marrow counts, and a hepatic activity index.

15. The system of claim 13, wherein the image data comprises at least one of or more frames corresponding to images of the patient in a plane transverse to a long axis of the body of the patient.

16. The system of claim 13, wherein the hardware processor is further configured to combine a plurality of frames from the image data, said frames corresponding to planes transverse to a long axis of the body of the patient.

* * * * *

UNITED STATES PATENT AND TRADEMARK OFFICE
CERTIFICATE OF CORRECTION

PATENT NO.          : 9,155,513 B2
APPLICATION NO.     : 14/333370
DATED               : October 13, 2015
INVENTOR(S)         : Ghosh et al.

Page 1 of 1

It is certified that error appears in the above-identified patent and that said Letters Patent is hereby corrected as shown below:

In the claims

Column 22 line 22, Claim 9, change "patient." to --patient;--.

Column 22 line 65, Claim 9, change "patient" to --patient;--.

Signed and Sealed this
Ninth Day of August, 2016

Michelle K. Lee
*Director of the United States Patent and Trademark Office*